US012145861B2

(12) United States Patent
Qureshi et al.

(10) Patent No.: US 12,145,861 B2
(45) Date of Patent: Nov. 19, 2024

(54) WATER PURIFICATION PROCESS USING ZINC OXIDE NANOPARTICLES

(71) Applicant: Imam Abdulrahman Bin Faisal University, Dammam (SA)

(72) Inventors: Faiza Qureshi, Dammam (SA); Muhammad Nawaz, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 488 days.

(21) Appl. No.: 17/709,809

(22) Filed: Mar. 31, 2022

(65) Prior Publication Data
US 2022/0220001 A1 Jul. 14, 2022

Related U.S. Application Data

(62) Division of application No. 15/868,418, filed on Jan. 11, 2018, now Pat. No. 11,325,839.

(51) Int. Cl.
*C01G 9/02* (2006.01)
*A23K 20/20* (2016.01)
(Continued)

(52) U.S. Cl.
CPC ............. *C01G 9/02* (2013.01); *A23K 20/30* (2016.05); *A23K 50/10* (2016.05); *A23K 50/20* (2016.05);
(Continued)

(58) Field of Classification Search
CPC .......... C01G 9/02; A23K 20/30; A23K 50/10; A23K 50/20; A23K 50/40; A23K 50/50; A23L 33/16; A61K 9/14; A61K 33/30; A61P 35/00; B01J 20/06; B01J 20/28007; B01J 20/28019; B01J 20/28059; B01J 23/06; B01J 35/23; B01J 35/30; B01J 35/39; B01J 35/51; B01J 35/612; B01J 35/613; B01J 35/633; B01J 35/647; B01J 37/009; B01J 37/031; C02F 1/00;
(Continued)

(56) References Cited

U.S. PATENT DOCUMENTS

| 8,512,672 B2 | 8/2013 | Lee et al. |
| 2010/0034730 A1 | 2/2010 | Lu et al. |
| 2015/0335744 A1 | 11/2015 | Petty |

FOREIGN PATENT DOCUMENTS

| CN | 1548376 A | 11/2004 |
| CN | 102627312 A | 8/2012 |

(Continued)

OTHER PUBLICATIONS

Mayekar, J., et al., "Role of Salt Precursor in the Synthesis of Zinc Oxide Nanoparticles", IJRET: International Journal of Research in Engineering and Technology, vol. 3, Issue 3, pp. 43-45, (Mar. 2014).
(Continued)

*Primary Examiner* — Madeline Gonzalez
(74) *Attorney, Agent, or Firm* — Oblon, McClelland, Maier & Neustadt, L.L.P.

(57) ABSTRACT

A method of using ZnO particles for the treatment of colon cancer and a method of using the particles for reducing the concentration of an organic contaminant in an aqueous solution is described. The ZnO particles are substantially spherical and may have nanopetals that provide a nano-flower morphology. The synthesis and characterization of the ZnO particles is also discussed.

11 Claims, 14 Drawing Sheets

(51) Int. Cl.

| | | |
|---|---|---|
| *A23K 50/10* | (2016.01) | |
| *A23K 50/20* | (2016.01) | |
| *A23K 50/40* | (2016.01) | |
| *A23K 50/50* | (2016.01) | |
| *A23L 33/16* | (2016.01) | |
| *A61K 9/14* | (2006.01) | |
| *A61K 33/30* | (2006.01) | |
| *A61P 35/00* | (2006.01) | |
| *B01J 20/06* | (2006.01) | |
| *B01J 20/28* | (2006.01) | |
| *B01J 23/06* | (2006.01) | |
| *B01J 35/00* | (2024.01) | |
| *B01J 35/08* | (2006.01) | |
| *B01J 35/10* | (2006.01) | |
| *B01J 35/23* | (2024.01) | |
| *B01J 35/30* | (2024.01) | |
| *B01J 35/39* | (2024.01) | |
| *B01J 35/51* | (2024.01) | |
| *B01J 35/61* | (2024.01) | |
| *B01J 35/63* | (2024.01) | |
| *B01J 35/64* | (2024.01) | |
| *B01J 37/00* | (2006.01) | |
| *B01J 37/03* | (2006.01) | |
| *C02F 1/00* | (2023.01) | |
| *C02F 1/28* | (2023.01) | |
| *C02F 1/30* | (2023.01) | |
| *C02F 1/32* | (2023.01) | |
| *C02F 1/72* | (2023.01) | |
| *C02F 101/30* | (2006.01) | |

(52) U.S. Cl.
CPC ............. *A23K 50/40* (2016.05); *A23K 50/50* (2016.05); *A23L 33/16* (2016.08); *A61K 9/14* (2013.01); *A61K 33/30* (2013.01); *A61P 35/00* (2018.01); *B01J 20/06* (2013.01); *B01J 20/28007* (2013.01); *B01J 20/28019* (2013.01); *B01J 20/28059* (2013.01); *B01J 23/06* (2013.01); *B01J 35/23* (2024.01); *B01J 35/30* (2024.01); *B01J 35/39* (2024.01); *B01J 35/51* (2024.01); *B01J 35/612* (2024.01); *B01J 35/613* (2024.01); *B01J 35/633* (2024.01); *B01J 35/647* (2024.01); *B01J 37/009* (2013.01); *B01J 37/031* (2013.01); *C02F 1/00* (2013.01); *C02F 1/281* (2013.01); *C02F 1/30* (2013.01); *C02F 1/32* (2013.01); *C02F 1/725* (2013.01); *A23V 2002/00* (2013.01); *C01P 2002/72* (2013.01); *C01P 2002/84* (2013.01); *C01P 2004/03* (2013.01); *C01P 2004/30* (2013.01); *C01P 2004/32* (2013.01); *C01P 2004/61* (2013.01); *C01P 2004/62* (2013.01); *C01P 2006/12* (2013.01); *C01P 2006/14* (2013.01); *C01P 2006/16* (2013.01); *C02F 2101/308* (2013.01); *C02F 2305/10* (2013.01)

(58) Field of Classification Search
CPC .... C02F 1/281; C02F 1/30; C02F 1/32; C02F 1/725; C02F 2101/308; C02F 2305/10; A23V 2002/00; C01P 2002/72; C01P 2002/84; C01P 2004/03; C01P 2004/30; C01P 2004/32; C01P 2004/61; C01P 2004/62; C01P 2006/12; C01P 2006/14; C01P 2006/16
USPC .......................... 210/748.13, 748.1, 748.14
See application file for complete search history.

(56) References Cited

FOREIGN PATENT DOCUMENTS

| CN | 102295307 B | 6/2013 |
|---|---|---|
| CN | 104445367 A | 3/2015 |

OTHER PUBLICATIONS

Jung, S., et al., "Sonochemical Preparation of Shape-Selective ZnO Nanostructures", Crystal Growth & Design, vol. 8, No. 1, 3 Pages total, (Nov. 30, 2007) (Abstract only).

Kataria N, Garg VK, Jain M, Kadirvelu K. Preparation, characterization and potential use of flower shaped Zinc oxide nanoparticles (ZON) for the adsorption of Victoria Blue B dye from aqueous solution. Advanced Powder Technology. Jul. 1, 2016;27(4): 1180-8. (Year: 2016).

Pasquet J, Chevalier Y, Couval E, Bouvier D, Noizet G, Morliere C, Bolzinger MA. Antimicrobial activity of zinc oxide particles on five micro-organisms of the Challenge Tests related to their physicochemical properties. International journal of pharmaceutics. Jan. 2, 2014; 460(1-2):92-100. (Year: 2014).

Ramani, Meghana, S. Ponnusamy, and C. Muthamizhchelvan. "From zinc oxide nanoparticles to microflowers: a study of growth kinetics and biocidal activity." Materials Science and Engineering: C 32.8 (2012): 2381-2389. (Year: 2012).

Applerot, Guy, et al. "Enhanced antibacterial activity of nanocrystalline ZnO due to increased ROS-mediated cell injury." Advanced Functional Materials 19.6 (2009): 842-852. (Year: 2009).

Kolodziejczak-Radzimska, Agnieszka, and Teofil Jesionowski. "Zinc oxide-from synthesis to application: a review." Materials 7.4 (2014): 2833-2881. (Year: 2014).

Sahu, Devashri, G. M. Kannan, and R. Vijayaraghavan. "Size-dependent effect of zinc oxide on toxicity and inflammatory potential of human monocytes." Journal of Toxicology and Environmental Health, Part A 77.4 (2014): 177-191. (Year: 2014).

Nair, Shantikumar, et al. "Role of size scale of ZnO nanoparticles and microparticles on toxicity toward bacteria and osteoblast cancer cells." Journal of Materials Science: Materials in Medicine 20.1 (2009): 235. (Year: 2009).

Moos, Philip J., et al. "ZnO particulate matter requires cell contact for toxicity in human colon cancer cells." Chemical research in toxicology 23.4 (2010): 733-739. (Year: 2010).

WATER PURIFICATION PROCESS USING ZINC OXIDE NANOPARTICLES

CROSS-REFERENCE TO RELATED APPLICATIONS

The present application is a Divisional of U.S. application Ser. No. 15/868,418, now allowed, having a filing date of Jan. 11, 2018.

BACKGROUND OF THE INVENTION

Technical Field

The present invention relates to a method of using ZnO particles to treat colon cancer and a method of using ZnO nanoflowers to reduce a concentration of an organic contaminant in an aqueous solution.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Zinc oxide (ZnO) is used for various purposes including as a white pigment, as a catalyst, as a constituent of anti-bacterial skin protection ointment, sunscreens, and wood varnishes. Zinc oxide is also known as wide band gap semiconductor and is well suited for emissive devices. Materials used for blocking UV radiation are required to be transparent to the visible part of the solar radiation while blocking the harmful UV radiation and zinc oxide is considered favorable in this regard.

However, many of the above applications use nano-scale zinc oxide, and little progress has been made in using zinc oxide particles on larger scales having different morphologies and increased surface areas. Though numerous processes are known for the synthesis of zinc oxide particles, such processes are not efficient and do not reliably produce zinc oxide particles with high surface areas or with attached nanostructures. This limitation is often a significant deterrent in exploring new uses of zinc oxide particles. In view of the foregoing, one objective of the present invention is to provide a method of using ZnO particles to treat colon cancer in a mammal and a method of using the particles to reduce a concentration of an organic contaminant in an aqueous solution by photocatalytic degradation and/or adsorption. The ZnO particles may be made by a specific synthesis route.

BRIEF SUMMARY OF THE INVENTION

According to a first aspect, the present disclosure relates to a method for treating a colon cancer in a mammal. This method involves administering, to the mammal, a therapeutically effective dose of ZnO particles having substantially spherical shapes with diameters of 220 nm-3.5 μm and BET surface areas of 8-25 $m^2/g$.

In one embodiment, the therapeutically effective dose is 0.1 to 5 g of ZnO particles per kg of the mammal per day.

In one embodiment, the diameters are 1.5-3.5 μm, and the BET surface areas are 15-25 $m^2/g$.

In one embodiment, the ZnO particles are porous with pore sizes of 20-35 nm.

In one embodiment, a surface of the ZnO particles has nanopetals of 50-200 nm thickness extending 100-500 nm from the surface, the nanopetals traversing the surface with lengths of 500 nm-2 μm.

In one embodiment, the ZnO particles are administered as a part of a composition, wherein the composition further comprises a food product, a pharmaceutically acceptable excipient, a pharmaceutically acceptable carrier, or an antioxidant.

In one embodiment, the mammal is a human, a non-human primate, a dog, a cat, a horse, a cow, a goat, a rat, a pig, a rabbit, or a mouse.

In one embodiment, the ZnO particles consist essentially of ZnO.

In one embodiment, the ZnO particles contact a first population of colon cancer cells in the colon cancer. At a time 24 hours after the contacting, the first population has a growth inhibition of 60-80% in relation to a second population of colon cancer cells in the colon cancer that were not contacted.

According to a second aspect, the present disclosure relates to a method of reducing an organic contaminant concentration in an aqueous solution. This method involves contacting ZnO nanoflowers with the aqueous solution comprising the organic contaminant at a contaminant concentration of 1 mg/L-1 g/L and irradiating the ZnO nanoflowers while in contact with the solution. Here, the ZnO nanoflowers have a generally spherical shape with a diameter of 1.5-3.5 μm. A surface of the ZnO nanoflowers has nanopetals of 50-200 nm thickness extending 100-500 nm from the surface, and these nanopetals traverse the surface with lengths of 500 nm-2 μm. The ZnO nanoflowers reduce the contaminant concentration in the solution by adsorption and/or photocatalytic degradation.

In one embodiment, the ZnO nanoflowers are dispersed within the solution at a concentration of 0.5-100 mg/L.

In one embodiment, the irradiating is 15-30 minutes of UV light irradiation, and the concentration of the organic contaminant after the irradiating is 40-50% of the concentration of the organic contaminant before the irradiating.

In one embodiment, the organic contaminant is at least one selected from the group consisting of pharmaceutical compound, a dye, a metabolite, a microbial toxin, an herbicide, a pesticide, and a steroid.

In one embodiment, the ZnO nanoflowers are made by heating an aqueous $Zn^{2+}$ solution with sodium hydroxide.

In one embodiment, the aqueous $Zn^{2+}$ solution comprises $Zn(NO_3)_2$.

In one embodiment, the ZnO nanoflowers consist essentially of ZnO.

In one embodiment, the ZnO nanoflowers have a band gap energy of 2.90-3.31 eV.

In one embodiment, the irradiating uses sunlight as an irradiation source.

In one embodiment, the method further comprises contacting the solution with a second absorbent or a second photocatalyst to reduce the concentration of the contaminant and/or reduce a concentration of a second contaminant in the solution.

In one embodiment, the method also involves rinsing the ZnO nanoflowers to produce cleaned ZnO nanoflowers and reusing the cleaned ZnO nanoflowers, which maintain a contaminant reduction capacity for at least 5 purification cycles.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
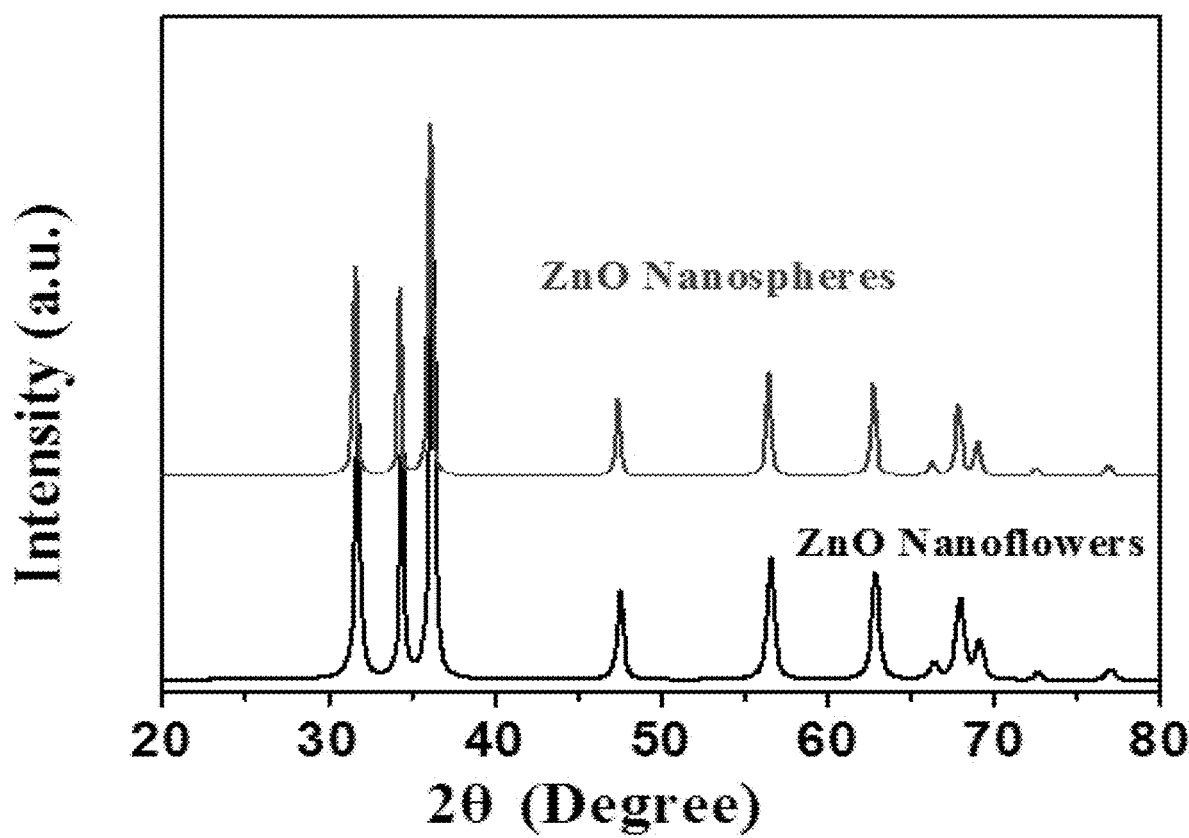
FIG. 1 is an X-ray diffraction pattern of ZnO nanoflowers and ZnO nanospheres.

Embodiments of the present disclosure will now be described more fully hereinafter with reference to the accompanying drawings, in which some, but not all embodiments of the disclosure are shown.

The present disclosure will be better understood with reference to the following definitions. As used herein, the words "a" and "an" and the like carry the meaning of "one or more." Within the description of this disclosure, where a numerical limit or range is stated, the endpoints are included unless stated otherwise. Also, all values and subranges within a numerical limit or range are specifically included as if explicitly written out.

For polygonal shapes, the term "diameter," as used herein, and unless otherwise specified, refers to the greatest possible distance measured from a vertex of a polygon through a central region of the face to the vertex on the opposite side. For a circle, an oval, and an ellipse, "diameter" refers to the greatest possible distance measured from one point on the shape through the centroid of the shape to a point directly across from it.

As used herein, "compound" is intended to refer to a chemical entity, whether as a solid, liquid, or gas, and whether in a crude mixture or isolated and purified.

In addition, the present disclosure is intended to include all isotopes of atoms occurring in the present compounds and complexes. Isotopes include those atoms having the same atomic number but different mass numbers. By way of general example and without limitation, isotopes of hydrogen include deuterium and tritium. Isotopes of carbon include $^{13}C$ and $^{14}C$. Isotopes of oxygen include $^{16}O$, $^{17}O$, $^{18}O$, and others. Isotopes of zinc include, but are not limited to, $^{64}Zn$, $^{66}Zn$, $^{67}Zn$, $^{68}Zn$, and $^{70}Zn$. Isotopically-labeled compounds of the disclosure can generally be prepared by conventional techniques known to those skilled in the art or by processes analogous to those described herein, using an appropriate isotopically-labeled reagent in place of the non-labeled reagent otherwise employed. In addition, where compounds have hydration states, any degree or mixture of hydration states may be used.

The present disclosure relates to methods of using ZnO particles. Here, the ZnO particles have substantially spherical shapes with diameters of 220 nm-3.5 µm, preferably 230 nm-500 nm, more preferably 250 nm-320 nm, or preferably 1.5 µm-3.5 µm, more preferably 2.2 µm-3.5 µm. As defined here, the term "substantially spherical" means that the standard deviation of the distance from anywhere on the outer surface to the particle centroid (center of mass) varies by less than 30%, preferably by less than 20%, more preferably by less than 10% of the average distance.

In one embodiment, the ZnO particles are monodisperse, having a coefficient of variation or relative standard deviation, expressed as a percentage and defined as the ratio of the particle diameter standard deviation (σ) to the particle diameter mean (µ), multiplied by 100%, of less than 25%, preferably less than 10%, preferably less than 8%, preferably less than 6%, preferably less than 5%. In a preferred embodiment, the ZnO particles are monodisperse having a particle diameter distribution ranging from 80% of the average particle diameter to 120% of the average particle diameter, preferably 85-115%, preferably 90-110% of the average particle diameter. In another embodiment, the ZnO particles are not monodisperse.

The ZnO particles may have BET surface areas of 8-25 $m^2/g$, preferably 15-24 $m^2/g$, more preferably 18-23 $m^2/g$, or preferably 8-15 $m^2/g$, more preferably 9-12 $m^2/g$. Here, the surface area may be determined by Brunauer-Emmett-Teller (BET) analysis of $N_2$ adsorption isotherms, though other techniques may be used, such as mercury intrusion porosimetry.

In one embodiment, the ZnO particles are porous with pore sizes of 20-35 nm, preferably 21-26 nm, more preferably 22-24 nm, or preferably 26-33 nm, more preferably 28-32 nm. The ZnO particles may have pore volumes of 0.05-0.16 $cm^3/g$, preferably 0.06-0.11 $cm^3/g$, more preferably 0.07-0.09 $cm^3/g$, or 0.10-0.15 $cm^3/g$, more preferably 0.11-0.14 $cm^3/g$.

In one embodiment, the ZnO particles may be present as agglomerates. As used herein, the term "agglomerates" refers to a clustered particulate composition comprising primary particles, the primary particles being aggregated together in such a way so as to form clusters thereof, at least 50 volume percent of the clusters having a mean diameter that is at least 2 times the mean diameter of the primary particles, and preferably at least 90 volume percent of the clusters having a mean diameter that is at least 5 times the mean diameter of the primary particles. The primary particles may be the ZnO particles having a mean diameter as those diameters previously described.

In one embodiment, the ZnO particles consist essentially of ZnO. As defined here, the ZnO particles consisting essentially of ZnO means that 95-100%, preferably 96.0-99.7%, more preferably 97.5-99.5% of the mass of ZnO particles is ZnO. Where the ZnO particles consist of less than 100% ZnO, the ZnO particles may have adsorbed, reacted, or incorporated contaminants, for instance from gas molecules, other metals or metal oxides, or organic compounds. In an alternative embodiment, the ZnO particles may be intentionally modified or mixed with other compounds. For example, the particles may be formed as a mixture of ZnS and ZnO at a molar ratio of 100:1-1:100, preferably 10:1-1:10, more preferably 4:1-1:4. As another example, the surface of ZnO particles may be decorated with other nanoparticles, for instance, $CeO_2$ or $V_2O_5$ nanoparticles having diameters of 30-100 nm, preferably 40-90 nm, more preferably 50-80 nm. In another embodiment, the ZnO particles may comprise Zn metal.

The ZnO particles may comprise ZnO in the form an amorphous phase, a crystalline phase, or both. Crystalline ZnO may be in a hexagonal wurtzite phase or a cubic zincblende phase, where in both cases the zinc and oxygen centers are tetrahedral. Preferably the ZnO is present in the wurtzite phase.

Figure 3A:
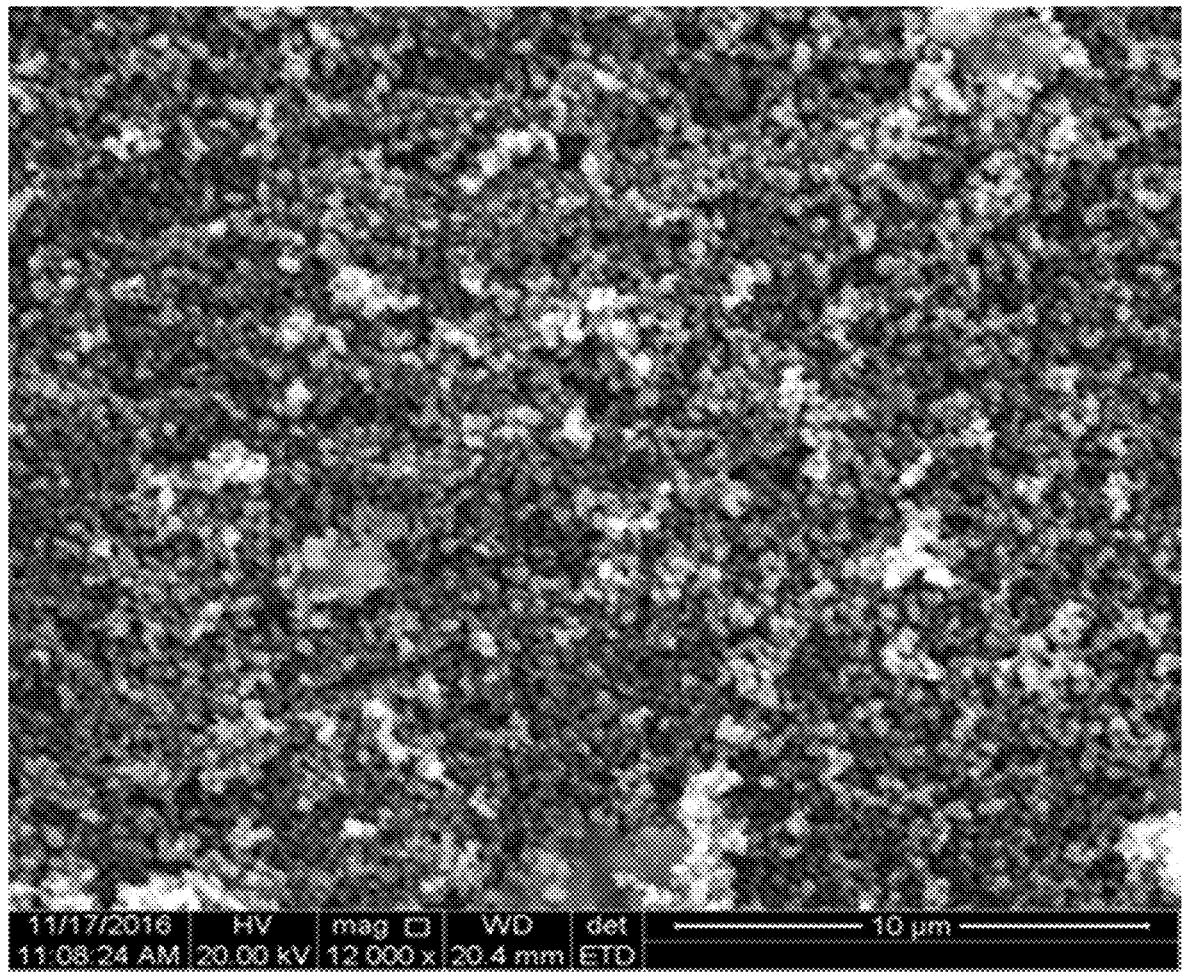
FIG. 3A is an SEM image of ZnO nanoflowers, scale bar 10 µm.
Figure 3B:
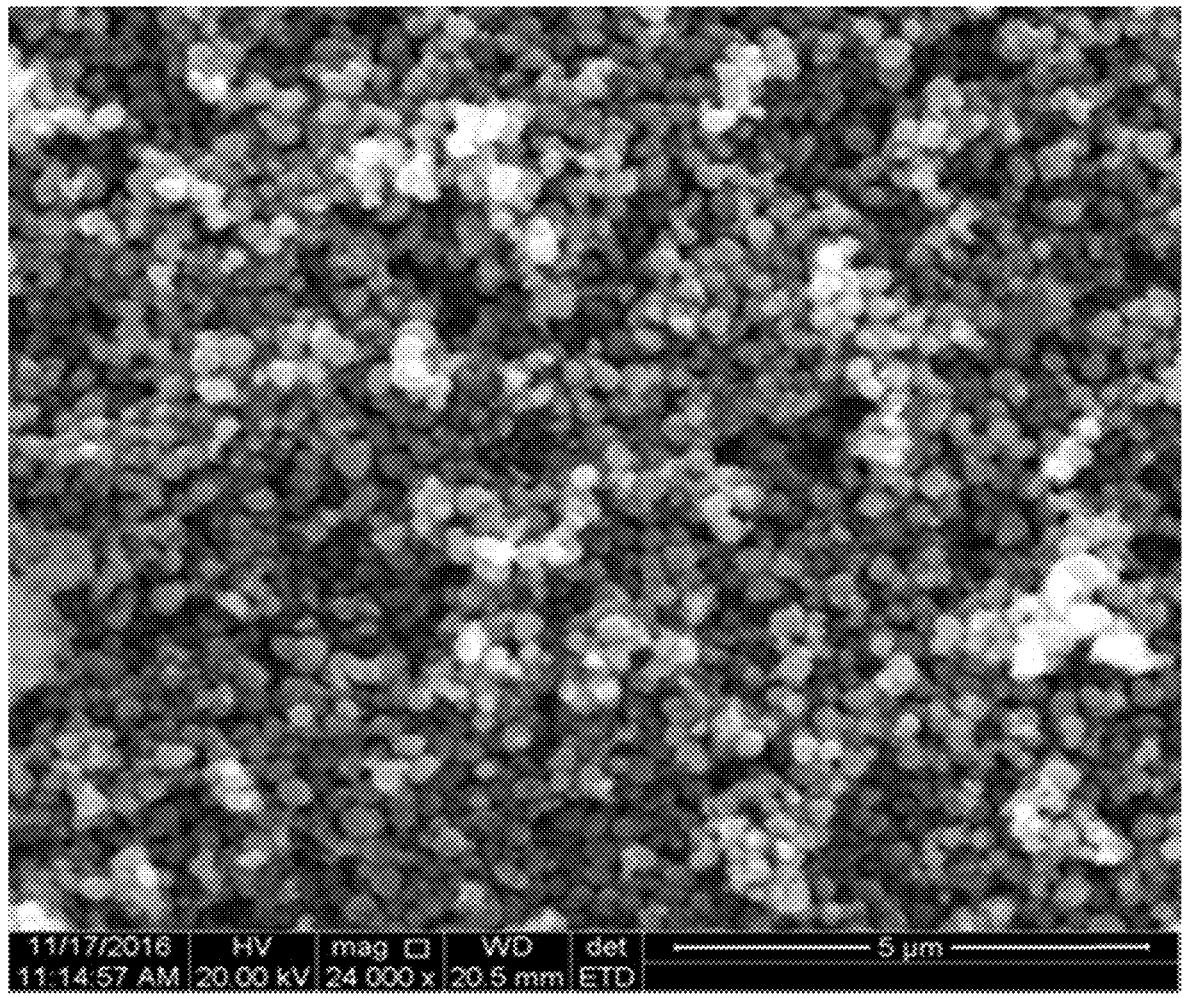
FIG. 3B is a zoomed-in view of FIG. 3A, scale bar 5 µm.

The ZnO particles may be further classified as ZnO nanospheres and ZnO nanoflowers based on size and morphology. The ZnO nanospheres have diameters of 220-500 nm, preferably 230-400 nm, more preferably 240-350 nm and BET surface areas of 8-15 $m^2/g$, preferably 8.5-12 $m^2/g$, more preferably 8.5-11 $m^2/g$. The ZnO nanospheres may have pore sizes of 26-35 nm, preferably 28-33 nm, more preferably 29-32 nm and pore volumes of 0.05-0.11 $cm^3/g$, preferably 0.06-0.10 $cm^3/g$, more preferably 0.07-0.09 $cm^3/g$. The SEM images of FIGS. 3A and 3B show examples of ZnO particles that are ZnO nanospheres. In some embodiments, the ZnO nanospheres as described above may be called "microspheres."

The ZnO nanoflowers may have diameters of 1.5-3.5 μm, preferably 2.2 μm-3.4 μm, even more preferably 2.3-3.3 μm, and BET surface areas of 15-25 $m^2/g$, preferably 18-24 $m^2/g$, more preferably 20-23 $m^2/g$. In other embodiments, the ZnO nanoflowers may have smaller diameters, such as diameters of 500 nm-1.5 μm, preferably 600 nm-1 μm, more preferably 650-900 nm. The ZnO nanoflowers may have pore sizes of 20-26 nm, preferably 21-25 nm, more preferably 22-24 nm and pore volumes of 0.10-0.15 $cm^3/g$, preferably 0.11-0.14 $cm^3/g$, more preferably 0.12-0.14 $cm^3/g$.

Figure 2A:
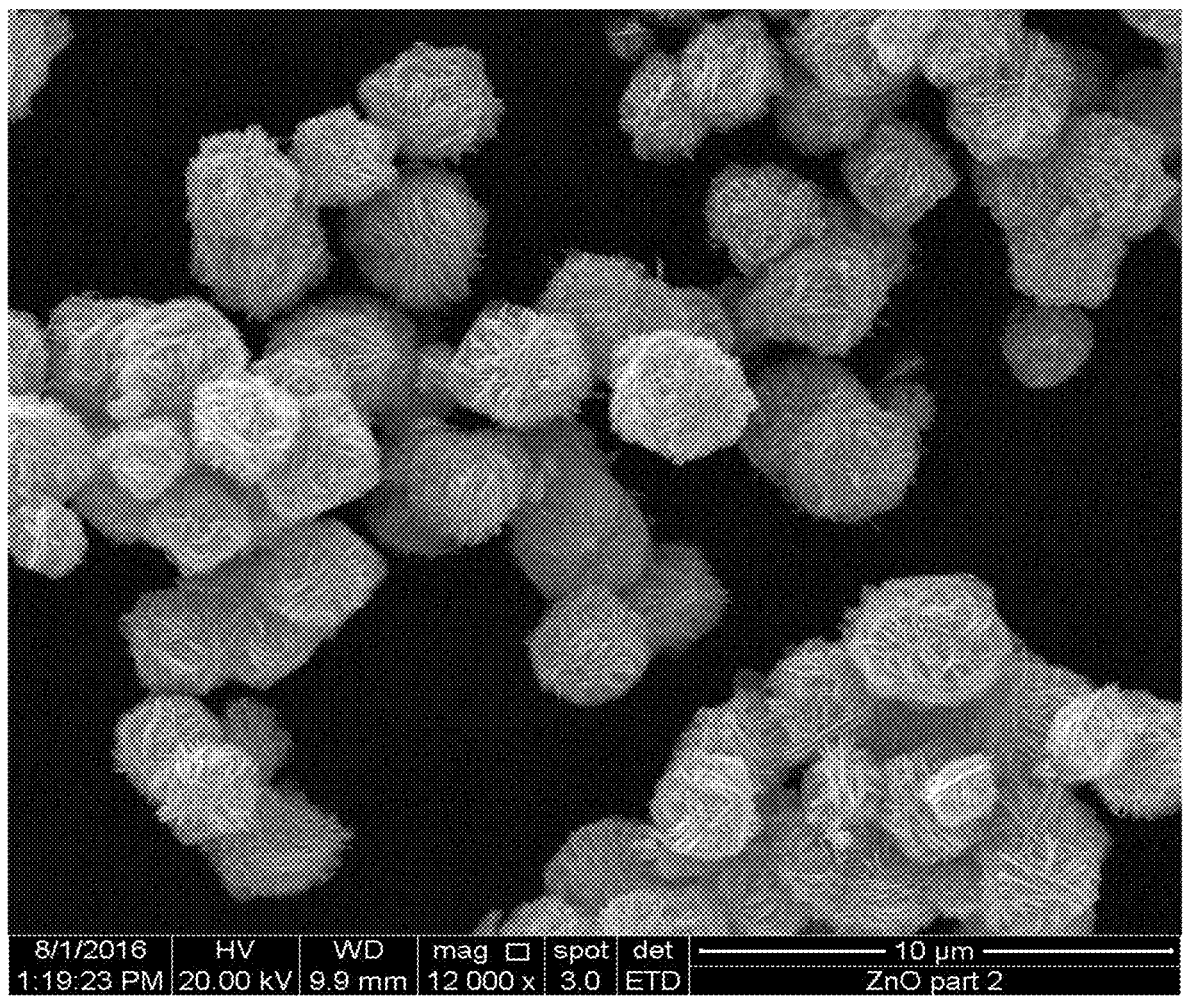
FIG. 2A is an SEM image of ZnO nanoflowers, scale bar 10 µm.
Figure 2B:
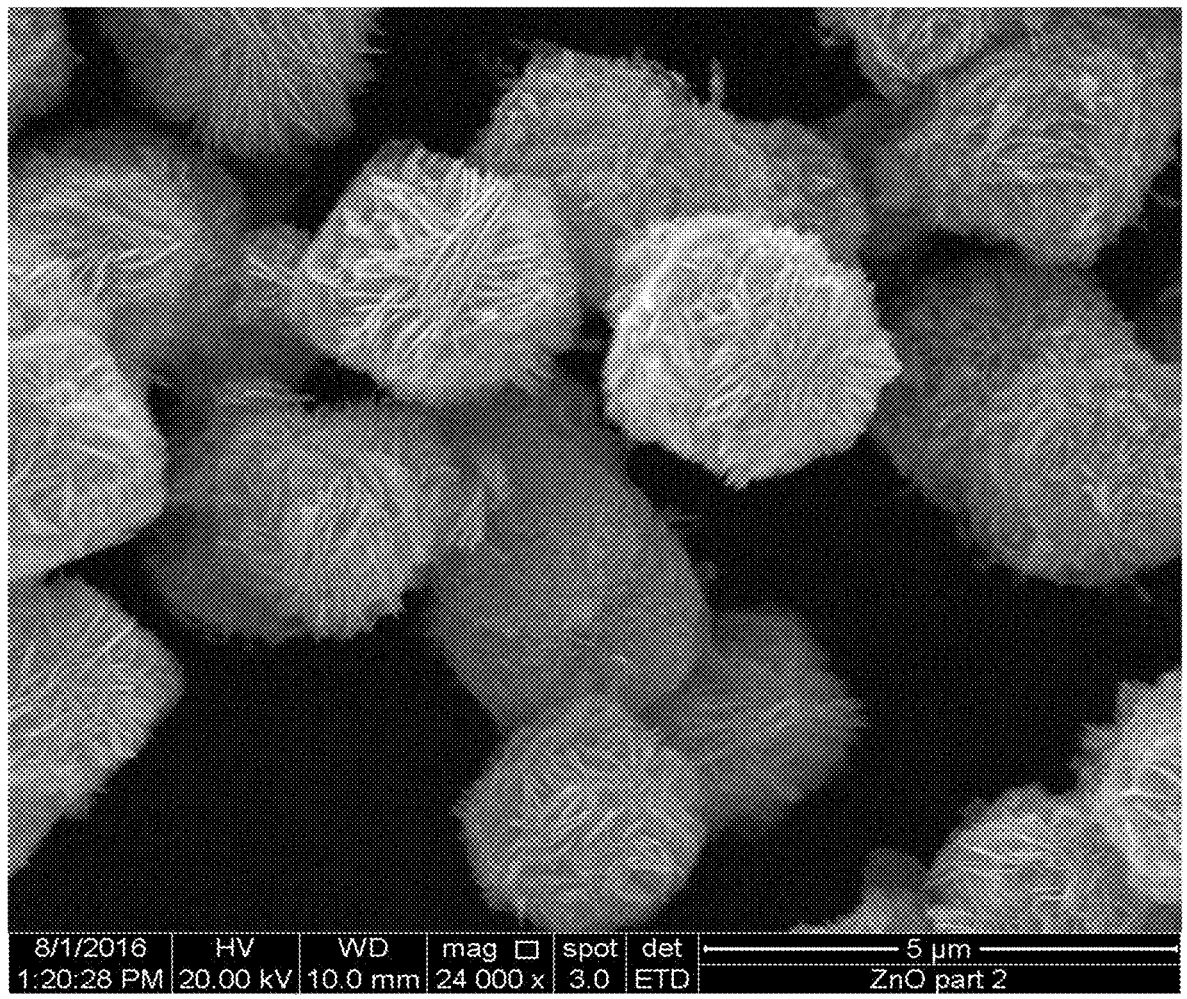
FIG. 2B is a zoomed-in view of FIG. 2A, scale bar 5 µm.

In one embodiment, a surface of the ZnO nanoflowers has nanopetals of 50-200 nm thickness, preferably 70-150 nm thickness, more preferably 85-120 nm thickness. In some embodiments, the nanopetals may instead be called nanosheets or nanoplatelets. The nanopetals may extend 100-500 nm from the surface, preferably 150-400 nm from the surface, more preferably 180-350 nm from the surface. The nanopetals may traverse the surface with lengths of 500 nm-2 μm, preferably 800 nm-1.5 μm, more preferably 900 nm-1.2 μm. In one embodiment, 70-100%, more preferably 80-99%, more preferably 85-97% of the outer surface of the nanoflowers is covered with nanopetals. In alternative embodiments, a ZnO nanoflower may have a lower coverage of nanopetals, or nanopetals that are shorter or longer in one or more dimensions. The SEM images of FIGS. 2A and 2B show examples of ZnO particles that are ZnO nanoflowers.

In an alternative embodiment, a ZnO particle that has a smaller diameter than a ZnO nanoflower may have nanopetals.

In some embodiments, the ZnO nanoflowers as described above may be called "microflowers."

In one embodiment, the ZnO nanoflowers and ZnO nanospheres have a band gap energy of 2.90-3.31 eV, preferably 2.95-3.15 eV, more preferably 3.00-3.12 eV, even more preferably 3.05-3.11 eV, though in some embodiments, the ZnO nanoflowers or ZnO nanospheres may have a band gap energy less than 2.90 eV or greater than 3.31 eV. In one embodiment, the band gap energy is 3.07-3.09 eV, or about 3.08 eV. The band gap energy may be determined by UV-Vis adsorption or some other method.

In one embodiment, the ZnO particles, including both ZnO nanospheres and ZnO nanoflowers, may be synthesized by heating an aqueous $Zn^{2+}$ solution with sodium hydroxide. The sodium hydroxide (NaOH) may be present in the aqueous $Zn^{2+}$ solution at a mass percentage of 0.5-1.5 mass %, preferably 0.6-1.2 mass %, more preferably 0.9-1.1 mass %, relative to the combined mass of aqueous $Zn^{2+}$ solution and sodium hydroxide. The $Zn^{2+}$ may be present at a mass percentage of 0.11-0.33 mass %, preferably 0.13-0.26 mass %, more preferably 0.20-0.24 mass %, relative to the combined mass of aqueous $Zn^{2+}$ solution and sodium hydroxide. In alternative embodiments, a different inorganic base may be used instead of NaOH, for instance, $Ca(OH)_2$, KOH, or LiOH. The aqueous $Zn^{2+}$ solution may be made by mixing a zinc salt in water, for instance, $ZnCl_2$, $Zn(NO_3)_2$, $ZnSO_4$, $ZnBr_2$, or some other zinc salt. Preferably, the zinc salt is $Zn(NO_3)_2$. In one embodiment, the $Zn^{2+}$ comes from mixing $Zn(NO_3)_2$ in water, including $Zn(NO_3)_2$ originally in an anhydrous form or a hydrated form (e.g. $Zn(NO_3)_2 \cdot 6H_2O$).

To synthesize ZnO nanospheres having the sizes and morphologies as described previously, the mixture of aqueous $Zn^{2+}$ solution and NaOH may be heated in an autoclave for 6-48 hours, preferably 12-36 hours, more preferably about 24 hours, at a temperature of 100-180° C., preferably 120-160° C., more preferably 130-150° C. to form precipitated ZnO. The reaction solution may be stirred during the heating. Preferably the autoclave surface in contact with the solution is coated with or comprises a non-reactive material, such as PTFE. The solution may be cooled to room temperature or about 20-28° C., preferably 23-27° C. The ZnO may be recovered from the solution by filtration and/or centrifugation, and washed with water and/or an alcohol. The washed ZnO may be dried in an oven for 16-32 hours, preferably 20-28 hours at a temperature of 50-80° C., preferably 55-70° C., to form ZnO nanospheres.

To synthesize ZnO nanoflowers having the sizes and morphologies as described previously, the mixture of aqueous $Zn^{2+}$ solution and NaOH may be heated or refluxed for 3-7 hours, preferably 4-6 hours, more preferably about 5 hours, at a temperature of 60-100° C., preferably 70-90° C., more preferably 75-85° C. to form precipitated ZnO. Preferably the reaction solution is stirred during the heating or refluxing. The solution may be cooled to room temperature or about 20-28° C., preferably 23-27° C. The ZnO may be recovered from the solution by filtration and/or centrifugation, and washed with water and/or an alcohol. The washed ZnO may be dried in an oven for 16-32 hours, preferably 20-28 hours at a temperature of 50-80° C., preferably 55-70° C. to form ZnO nanoflowers.

In alternative embodiments, ZnO nanospheres or ZnO nanoflowers having sizes and morphologies as described above may be synthesized through completely different processes.

According to a first aspect, the present disclosure relates to a method for treating a colon cancer in a mammal. This method involves administering a therapeutically effective dose of ZnO particles. The ZnO particles may have the sizes and morphologies as described above, and may be present as ZnO nanoflowers and/or ZnO nanospheres.

In a preferred embodiment, the cancer is colon cancer. However, in other embodiments, the cancer may be breast cancer, liver cancer, colorectal cancer, stomach cancer, skin cancer, prostate cancer, ovarian cancer, testicular cancer, renal cancer, brain cancer, lung cancer, uterine cancer, bladder cancer, esophageal cancer, or pancreatic cancer. The cancer may be an adenocarcinoma, a basal cell carcinoma, a squamous cell carcinoma, a renal cell carcinoma, a ductal carcinoma in situ (DCIS), an invasive ductal carcinoma, a transitional cell carcinoma, a soft tissue sarcoma, or leukemia. In one embodiment, the mammal is a human, a non-human primate, a dog, a cat, a horse, a cow, a goat, a rat, a pig, a rabbit, or a mouse. Preferably the mammal is a human.

A "therapeutically effective dose" refers to an amount of the ZnO particles being administered which will relieve to some extent one or more of the symptoms of the cancer being treated. In another embodiment, a "therapeutically effective dose" refers to the amount which has the effect of inhibiting (that is, slowing to some extent, or preferably stopping) cancer cell growth or proliferation. Similarly, the phrase "treat a cancer in a mammal" refers to administering a therapeutically effective dose of the ZnO particles to a mammal.

As used herein, the terms "treat", "treatment", and "treating," in the context of the administration of a therapeutically effective dose of the ZnO particles to a mammal, refer to the reduction or inhibition of the progression and/or duration of a cancer, the reduction or amelioration of the severity of the cancer, and/or the amelioration of one or more symptoms thereof resulting from the administration of one or more therapies. "Treating" or "treatment" of the cancer includes preventing the cancer from occurring in a subject that may be predisposed to the cancer but does not yet experience or exhibit symptoms of the cancer (prophylactic treatment), inhibiting the cancer (slowing or arresting its development), ameliorating the cancer, providing relief from the symptoms or side-effects of the cancer (including palliative treatment), and relieving the cancer (causing regression of the cancer). With regard to the cancer, these terms simply mean that one or more of the symptoms of the cancer will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in cancer-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

In one embodiment, the ZnO particles are administered as a part of a composition, wherein the composition further comprises a food product, a pharmaceutically acceptable excipient, a pharmaceutically acceptable carrier, or an antioxidant.

In one embodiment of the method, the composition may comprise a food product. The food product may be an ingredient to improve a flavor or appearance of the ZnO particles for oral administration, such as sugar, food coloring, non-nutritive sweeteners, preservatives, artificial flavoring, or natural flavoring. In one embodiment, the food product may be a snack or candy, such as dried fruit, a lozenge, fruit leather, yogurt, pudding, a gummy, an energy bar, a candy bar, or a chewing gum. In other embodiments, the food product may be a drink, such as tea, water, milk, smoothie, soft drink, or shake. In other embodiments, the food product may be a food that is part of a meal. In one embodiment, the food product may comprise 0.01-50 mass %, preferably 0.1-10 mass %, more preferably 0.2-1.0 mass % ZnO particles relative to a combined mass of the ZnO particles and food product. However, in some embodiments, the food product may comprise less than 0.01 mass % or more than 50 mass % ZnO particles.

In one embodiment, the composition comprises 1-99.9%, preferably 10-99.9%, more preferably 20-99.9%, more preferably 30-99.9%, more preferably 40-99.9%, more preferably 50-99.9%, more preferably 60-99.9%, more preferably 70-99.9%, more preferably 80-99.9%, even more preferably 90-99.9% of ZnO particles, and 0.1% or more of the pharmaceutically acceptable carrier or excipient, based on the total weight of the composition.

In one embodiment, the pharmaceutically acceptable carrier or excipient is a dispersing agent, a disintegrating agent, a binding agent, or a lubricating agent.

In one embodiment, the pharmaceutically acceptable carrier or excipient may be a sugar, such as lactose, glucose, or sucrose; cellulose, or its derivatives, such as sodium carboxymethyl cellulose, ethyl cellulose and cellulose acetate; starches, such as corn starch, tapioca starch, and potato starch; crospovidone, croscarmellose sodium, sodium starch glycolate, gelatin, alginate, carnauba wax, pregelatinized starch, xylitol, mannitol, sorbitol, polyethylene glycol, polyvinylpyrrolidone, talc, silica, sodium stearyl fumarate, magnesium stearate, stearic acid, sodium benzoate, sodium lauryl sulfate, mineral oil, palmitic acid, or mixtures thereof.

In one embodiment, the composition is formulated for local or systemic effect, and may be administered by topical, enteral, or parenteral routes. Modes of administration may include, but are not limited to, transdermal administration, eye drops, ear drops, oral administration, intravenous administration, topical administration, inhalation spray, rectal administration, intradermal administration, transdermal administration, subcutaneous administration, intramuscular administration, intralesional administration, intrapulmonal administration, epidural administration, intravesical administration, intracranial administration, intracardial administration, intrasternal administration and sublingual administration.

In one embodiment the composition is in solid, semi-solid, or liquid dosage forms. Tn solid dosage forms for oral administration (including but not limited to capsules, tablets, pills, powders, and granules), the composition is mixed with one or more pharmaceutically acceptable carriers or excipients such as: (1) fillers or extenders, such as starches, lactose, sucrose, glucose, mannitol, and silicic acid; (2) binders, such as carboxymethylcellulose, alginate, gelatin, polyvinyl pyrrolidone, and sucrose; (3) humectants, such as glycerol; (4) disintegrating agents, such as alginate, calcium carbonate, potato or tapioca starch, silica, and sodium carbonate; (5) solution retarding agents, such as paraffin; (6) absorption accelerators, such as quaternary ammonium compounds; (7) wetting agents, such as acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents.

Semi-solid dosage forms may be used for topical administration and may include sprays, ointments, pastes, creams, lotions, gels, and patches. These forms may further include pharmaceutically acceptable carriers or excipients such as animal and vegetable fats, oils, waxes, paraffins, starch, tragacanth, cellulose derivatives, polyethylene glycols, silicones, bentonites, silicic acid, talc, and zinc oxide.

Liquid dosage forms for oral administration include pharmaceutically acceptable emulsions, microemulsions, solutions, suspensions, syrups, and elixirs. The liquid dosage forms may also contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

In one embodiment of the method, the ZnO particles are administered as a part of a composition which further comprises an antioxidant. The antioxidant may be melatonin, lutein, α-carotene, β-carotene, astaxanthin, tocotrienol, tocopherol, ascorbic acid, gallic acid, ellagic acid, or lycopene. The weight ratio of the antioxidant to the ZnO particles may be 1:65,000-1:1, preferably 1:10,000-1:100, more preferably 1:5,000-1:500. However, in other embodiments, the antioxidant may be administered at a greater mass than the ZnO particles.

In one embodiment, the therapeutically effective dose is 0.1-5 g, preferably 1.0-4.0 g, more preferably 1.5-2.5 g of ZnO particles per kg of the mammal per day. In another embodiment, the therapeutically effective dose may be 0.1-1 g, 1-2 g, 2-3 g, 3-4 g, or 4-5 g of ZnO particles per kg of the mammal per day. In other embodiments, the therapeutically effective dose may be less than 0.1 g or more than 5 g of ZnO particles per kg of the mammal per day. In one embodiment, the administration of a therapeutically effective dose of ZnO particles may be split or distributed over a single day. For example, a 1 g per kg per day dose could be split into two separate doses of 0.5 g per kg, and administered at two different times in a day, for example, 8 AM and 7 PM. Or, a 1 g per kg per day dose could be split into four separate doses of 0.25 g per kg, and administered at four different times in a day. In a related embodiment, a daily dose may be a combined dose administered less frequently than every day. For example, a 0.75 g per kg per day dose could be administered as a 1.5 g per kg dose every other day. In certain embodiments, the dose may be continually administered throughout an entire day or a part of a day, such as by intravenous administration. Where a dose is administered continuously throughout part of the day, it may be administered for 2-18 h, or 4-16 h.

A person having ordinary skill in the art may be able to adjust administration based on the changes in expression levels of one or more biomolecules. These biomolecules may be measured from a patient's blood serum. These biomolecules include, but are not limited to carcinoembryonic antigen (CEA), carbohydrate antigen 19-9 (CA19-9), MAPKAPK3, ACVR2B, and/or circulating DNA markers for K-ras mutations. For example, a human patient with colon cancer who is administered the ZnO particles at a dosage of 1 g per kg bodyweight per day for 3 months may show serum levels of CEA decrease by 15% as compared to before the administering. The daily dosage may be increased to 2 g per kg bodyweight to cause a desired 30-70% decrease in CEA serum levels. A normal serum concentration of CEA is ≤3 ng/mL, and for example, a cancer patient may have a concentration of about 10 or about 30 ng/mL. In other embodiments, a percent change in enzyme activity or biomolecule expression level may warrant modifications to other treatment methods, such as other supplements, chemotherapy, or other cancer treatments.

In one embodiment, the ZnO particles may be administered in conjunction with other forms of cancer treatment, such as radiation therapy or chemotherapy. Preferably the ZnO particles may be administered 1-4 weeks or 2-3 weeks before starting a chemotherapy regimen, and the administration would continue throughout the duration of the chemotherapy. The administering may be stopped at the same time as the other cancer treatment, or the ZnO particles may be administered for a longer period. It is envisioned that chemotherapy drugs may work synergistically with the ZnO particles. In one embodiment, the ZnO particles may be used as drug delivery vehicles, for example, to deliver and release compounds of a FOLFIRI-Bevacizumab treatment (chemotherapy regimen comprising ceucovorin calcium (folinic acid), fluorouracil, irinotecan hydrochloride, and bevacizumab (AVASTIN)).

In an alternative embodiment, cancer cells may be treated with the ZnO particles in vitro, for instance as a way to test the ZnO particles under different conditions in a controlled environment or with additional drugs. These cancer cells may come from a biopsy of a mammal, for instance a biopsy of a colon cancer, or the cells may be from an established cancer cell line, for instance, HCT 116, MDA-MB-231, MCF-7, AU565, BT20, HeLa, HepG2, SNU-475, LH86, Caco-2, NCI-H250, A-498, Eph4 1424.2, SK-MES-1, DU 145, CHLA-02-ATRT, SCC-4, A-253, SNU-C2B, LS513, or some other cancer cell line. The cells may come from a cancer that formed on its own in a mammal, or may come from a cancer that was formed by chemical induction or radiation. Diethyl nitrosoamine, (DEN), 7,12-dimethylbenz[a]anthracene (DMBA), 12-O-tetradecanoylphorbol-13-acetate (TPA), azoxymethane (AOM), or some other carcinogenic compound may be used to chemically induce cancer. Additionally, the cancer cells may be derived from a tumor or cancer cells that were transplanted and allowed to grow in a mammal.

In one embodiment of the method, the ZnO particles contact a first population of colon cancer cells in the colon cancer. At a time 24 hours after the contacting, the first population has a growth inhibition of 60-80%, preferably 65-78%, more preferably 70-77% in relation to a second population of colon cancer cells in the colon cancer that were not contacted. However, in other embodiments, the growth inhibition may be lower than 60% or greater than 80%. As defined here, the growth inhibition is the percentage decrease in viability of the cell population upon treatment. The viability of a cell population is the percentage of living cells in relation to a second control cell population. The viability may be measured by a standard live/dead cell assay, such as an MTT assay, flow cytometry, by dyeing and manually counting cells, or by some other method. The viability may also be determined at a time earlier or later than 24 hours after the contacting.

In an alternative embodiment, given the photocatalytic activity of the ZnO particles, the method may further involve a step of irradiating the ZnO particles in contact with the colon cancer cells. This may be a type of photodynamic therapy (PDT).

According to a second aspect, the present disclosure relates to a method of reducing a concentration of an organic contaminant in an aqueous solution. This method involves contacting ZnO nanoflowers with the aqueous solution comprising the contaminant and irradiating the ZnO nanoflowers while in contact with the aqueous solution. The ZnO nanoflowers reduce the contaminant concentration in the aqueous solution by adsorption and/or photocatalytic degradation.

In one embodiment, the organic contaminant is at least one selected from the group consisting of pharmaceutical compound, a dye, a metabolite, a microbial toxin, an herbicide, a pesticide, and a steroid. In a preferred embodiment, the organic contaminant may be a dye. In a further embodiment, where the organic contaminant is a dye, the dye may be an azin dye, an azo dye, a diarylmethane dye, a fluorescent dye, a food coloring, a fuel dye, an ikat dye, an indigo structured dye, an indophenol dye, a perylene dye, a phenol dye, a quinoline dye, a rhodamine dye, a solvent dye, a staining dye, a thiazine dye, a thiazole dye, a triarylmethane dye, a vat dye, a violanthrone dye, or some other type of dye. In a preferred embodiment, the dye may be a azo dye, in particular, methyl orange (sodium 4-{[4-(dimethylamino)phenyl]diazenyl}benzene-1-sulfonate).

The organic contaminant may be present in the aqueous solution at a concentration of 1 mg/L-1 g/L, preferably 2 mg/L-500 mg/L, more preferably 5 mg/L-200 mg/L, though in some embodiments, the organic contaminant may be present in the aqueous solution at a concentration of less than 1 mg/L or greater than 1 g/L.

The aqueous solution may come from an ocean, a bay, a river, a lake, a swamp, a pond, a pool, a fountain, a bath, an aquarium, a water treatment plant, a sewage treatment plant, a desalination plant, a manufacturing plant, a chemical plant, a textile plant, a power plant, a gas station, a food processing plant, a restaurant, a dry cleaner, or some other place that may generate contaminated water mixtures. In another embodiment, the aqueous solution may be prepared in a laboratory or pilot plant for the purpose of testing contaminant removal. In some embodiments, the aqueous solution may be a brine, or comprise sea water or salt water.

In one embodiment, the aqueous solution may comprise a non-polar liquid phase at a volume percent concentration of 0.5-50%, preferably 2-40%, more preferably 4-30% relative to a total volume of the contaminated water mixture. The non-polar liquid phase may be emulsified or dispersed throughout the aqueous solution, may float at the top of the aqueous solution, or some combination of both. In another embodiment, the aqueous solution may not contain a non-polar liquid phase.

In one embodiment, the ZnO nanoflowers may be contacted with the aqueous solution for a period of time effective to reduce the contaminant concentration by 40-100%, preferably 50-99%, more preferably 60-95%. In one embodiment, this time may be 20-180 minutes, preferably 30-120 minutes, more preferably 40-105 minutes, though in some embodiments the time may be shorter than 20 minutes or longer than 180 minutes. In one embodiment, the ZnO nanoflowers may be contacted with the aqueous solution by dispersing the ZnO nanoflowers in a fixed volume of aqueous solution, and then stirring or agitating the aqueous solution to keep the ZnO nanoflowers evenly mixed throughout. In one embodiment, the ZnO nanoflowers are dispersed within the aqueous solution at a concentration of 0.5-100 mg/L, preferably 5-80 mg/L, more preferably 10-60 mg/L, though in some embodiments, the ZnO nanoflowers may be dispersed within the aqueous solution at a concentration of less than 0.5 mg/L or greater than 100 mg/L.

In one embodiment, the ZnO nanoflowers may not be dispersed in aqueous solution but fixed to a solid support, such as a plate or a wire mesh. In one embodiment, the solid support may be planar so that irradiated light may more evenly spread on the ZnO nanoflowers. The solid support may also be a single piece so that the ZnO nanoflowers can be easily removed from the aqueous solution, or removed from a vessel. In a further embodiment, where the ZnO nanoflowers are attached to a solid support so that they do not disperse, the aqueous solution may be continually flowed over the ZnO nanoflowers while irradiating. In another related embodiment, the aqueous solution may be intermittently flowed over the ZnO nanoflowers while irradiating. Alternatively, the ZnO nanoflowers may be dispersed but confined within a volume of wire mesh. In another embodiment, the ZnO nanoflowers may be fixed to a solid support, but dispersed in aqueous solution. For example, the ZnO nanoflowers may be attached to magnetic microparticles having diameters of 10-400 preferably 40-200 μm.

In one embodiment, the ZnO nanospheres may be used instead of ZnO nanoflowers in the second aspect of the disclosure for reducing the contaminant concentration in the aqueous solution by adsorption and/or photocatalytic degradation.

In an alternative embodiment, ZnO particles larger than ZnO nanoflowers, or smaller than the ZnO nanospheres, may be used in a similar procedure or arrangement for reducing the contaminant concentration in the aqueous solution by adsorption and/or photocatalytic degradation.

Preferably, the illuminating is with UV light. The UV light source may be a mercury or xenon gas discharge lamp, an electric arc, sunlight, a light emitting diode (LED), a laser, a fluorescent lamp, a cathode ray tube, or some other source. In one embodiment, filters, reflectors, collimators, fiber optics, polarizers, and/or lenses may be used to manipulate the light path or properties of the light from the light source. For example, one or more reflectors may be used to focus the light from a mercury gas discharge lamp onto ZnO nanoflowers fixed on a substrate or into an aqueous solution having dispersed ZnO nanoflowers. Alternatively, a reflector may be positioned opposite the light source in order to reflect stray UV light back towards the aqueous solution. In one embodiment, two or more light sources may be used, which may be of the same type or different types, and may be positioned on the same side or on different sides of the aqueous solution. As another example, where sunlight is used as a light source, the sunlight may be filtered, reflected, and focused into the aqueous solution to increase the proportion of UV light intensity while minimizing heating and radiation from other wavelengths. For instance, a Wood's glass optical filter may be used to allow UV light to pass while blocking other wavelengths. In one embodiment, a UV light source may also emit wavelengths longer than the UV range of 100-400 nm range, for instance, wavelengths of 405-420 nm.

In one embodiment, the UV light has an intensity of 450-1550 mW/cm$^2$, preferably 600-1400 mW/cm$^2$, more preferably 800-1200 mW/cm$^2$. However, in alternative embodiments, a lower intensity may be used if the flow rate is slowed or if the filtered water product is reapplied to the feed side coating. The UV light source may emit light within the wavelength range of 100-410 nm, preferably 370-405 nm, more preferably 390-400 nm. Depending on the composition and morphology of the photocatalyst used, certain UV wavelengths may be more preferable than others. Ideally, the UV wavelength corresponds to an energy equal to or greater than the electronic band gap energy of the ZnO nanoflowers.

In one embodiment, the ZnO nanoflowers reduce the contaminant concentration in the aqueous solution by photocatalytic degradation. Here, exposure of the ZnO nanoflowers to an irradiation of a wavelength corresponding to the band gap energy or a greater energy may cause the photoexcitation of ZnO electrons into a conduction band with a corresponding generation of holes in a valence band. The strong reduction power of the electrons and the strong oxidation power of the holes may lead to the decomposition of organic materials, preferably into harmless byproducts, which produces a reduced concentration of organic contaminant. In one embodiment, the ZnO nanoflowers may cause other reactions, such as hydrolysis and/or water splitting.

In one embodiment, a light source may be located outside of a vessel containing the aqueous solution, and may transmit UV light and/or other wavelengths through an additional opening in the vessel wall or through a transparent window in the vessel wall. For example, the transparent window may comprise quartz or a polymeric material transparent to UV light such as poly(methyl methacrylate) (also known as PLEXIGLAS). As defined herein, "transparent" refers to an optical quality of a compound wherein a certain wavelength or range of wavelengths of light may traverse through a portion of the compound with a small loss of light intensity. Here, the "transparent window" may causes a loss of less than 10%, preferably less than 5%, more preferably less than 2% of the intensity of a wavelength of UV light. In one embodiment, the vessel wall and transparent window may comprise the same material, for example, a vessel may comprise poly(methyl methacrylate) walls, which may also function as transparent windows. In another embodiment, a vessel wall may have a window that is partially transparent to UV light, for instance, a window comprising soda lime glass.

Where an irradiation source emits heat, the aqueous solution or a vessel containing the aqueous solution may be temperature-regulated to prevent overheating and/or evaporation, for example, by water tubing, a water and/or ice bath, ice packs, heat sinks, or by air cooling. Devices to measure and record the physical and/or chemical properties of the aqueous solution may be submerged in the aqueous solution or connected through a wall of a vessel containing the aqueous solution. Examples of these devices include, but are not limited to, pressure gauges, flowmeters, conductivity meters, pH meters, temperature sensors, and spectrophotometers.

In one embodiment, the ZnO nanoflowers may reduce the organic contaminant concentration by adsorption. Here, molecules of the organic contaminant adhere to the surface of the ZnO nanoflowers, on an outer exposed surface or within the nanopetals or pores. The adsorption may result from electrostatic attraction, physisorption, and/or chemisorption. In one embodiment, the ZnO nanoflowers may reduce the organic contaminant concentration only by adsorption. For instance, this condition may occur if the ZnO nanoflowers and aqueous solution are not exposed to light. In another embodiment, the ZnO nanoflowers may reduce the organic contaminant concentration substantially through photocatalytic degradation, for instance, under high intensity UV light or with short contact times. In another embodiment, the ZnO nanoflowers may reduce the organic contaminant concentration by both adsorption and photocatalytic degradation. In some cases, contaminant molecules may first adsorb to ZnO nanoflowers for a moment before being photocatalytically degraded. In other cases, a combination of both adsorption and photocatalytic degradation may cause a reduction in contaminant concentration. For example, 30-90%, preferably 40-80% of the total moles of contaminant removed from the aqueous solution may be a result of photocatalytic degradation, with the remaining moles being removed by adsorption. In one embodiment, sunlight may be used as the irradiation source in order to reduce the use of electricity.

The aqueous solution may or may not be pre-processed, for instance, by filtering through a coarse filter to remove large particulate matter, or by exposure to UV light or ozone. In one embodiment, the method further comprises contacting the aqueous solution with a second absorbent or a second photocatalyst to reduce the concentration of the contaminant and/or reduce a concentration of a second contaminant in the aqueous solution. This contacting with a second absorbent or photocatalyst may be done before, during, or after the step of mixing the ZnO nanoflowers with the aqueous solution. In one embodiment, the ZnO nanoflowers and the second absorbent or photocatalyst may be present in the same volume of aqueous solution simultaneously. In another embodiment, one may be mixed and then removed before the second is added. In another embodiment, one may be mixed, and then the other may be mixed together. In another embodiment, both ZnO nanoflowers and second absorbent or photocatalyst may be added and mixed together at the same time. The second absorbent or photocatalyst may be dispersed in the aqueous solution, fixed to a solid support, or confined on a packed bed. In another embodiment, an adsorbent may be used in place of the second absorbent.

In one embodiment, the irradiating is carried out for 15-30 minutes, preferably 18-28 minutes, more preferably 20-25 minutes, and the contaminant concentration after the irradiating is 40-50%, preferably 42-48%, or about 45% of the contaminant concentration before the irradiating. In a further embodiment, this irradiating is by UV light irradiation. In other embodiments, the irradiating may be carried out for shorter or longer times, and the contaminant concentration may be less than 40% or greater than 50% of the original concentration. These variations may depend on parameters including but not limited to the intensity and wavelength of the irradiation, the type of contaminant, the concentration of contaminant and/or ZnO nanoflowers, and the surface area of the ZnO nanoflowers. In an alternative embodiment, the UV light irradiation may directly photobleach, react, or degrade a contaminant without the contaminant having to contact the ZnO nanoflowers.

In one embodiment, the contaminant concentration may be determined by comparing the change in the UV-Vis absorbance at certain wavelengths. For example and without limitation, a contaminant that absorbs strongly at a wavelength of 465 nm may have its relative concentration change determined by observing the decrease in 465 nm absorbance. In a further embodiment, more than one wavelength may be monitored.

In one embodiment, the method also involves rinsing the ZnO nanoflowers to produce cleaned ZnO nanoflowers and reusing the cleaned ZnO nanoflowers, which maintain a contaminant reduction capacity for at least 5 purification cycles. In one embodiment, the ZnO nanoflowers may be removed or separated from the aqueous solution prior to the rinsing, by filtering, centrifugation, evaporation, decanting, or some other means. In one embodiment, the ZnO nanoflowers may be attached to a magnetic solid support, such as Fe microparticles, and the ZnO nanoflowers may be removed from aqueous solution by a permanent magnet or an electromagnet. Where the ZnO nanoflowers may be attached to a single solid support, such as a plate or a wire mesh, the entire support may be lifted from the aqueous solution, or the aqueous solution drained away from the support. Preferably the ZnO nanoflowers are rinsed with water, such as deionized or distilled water, and in some embodiments, the ZnO nanoflowers may be rinsed with an organic solvent such as chloroform, acetone, methanol, or ethanol. In a preferred embodiment, the ZnO nanoflowers are rinsed with deionized water. In one embodiment, the ZnO nanoflowers may be sonicated in water or some other solvent. Where the ZnO nanoflowers are rinsed with an organic solvent, preferably the ZnO nanoflowers are subsequently dried or rinsed with water in order to remove the organic solvent.

As used herein, "maintains a contaminant reduction capacity" means that under substantially identical conditions (ZnO nanoflower concentration, contact time, contaminant type and concentration, irradiation, etc.) reused ZnO nanoflowers are able to decrease a contaminant concentration by an amount that is within 70%, preferably within 80%, more preferably within 90% of its initial decrease in contaminant concentration. In some instances, the ZnO nanoflowers may have greater contaminant reduction capacities given longer contact times.

A purification cycle refers to the adsorption and/or photocatalytic degradation of a contaminant by the ZnO nanoflowers and the subsequent rinsing of the ZnO nanoflowers to produce cleaned ZnO nanoflowers. Preferably the cleaned ZnO nanoflowers are able to maintain their contaminant reduction capacity across different contaminants. In other embodiments, the cleaned ZnO nanoflowers are able to maintain their adsorption capacity for at least 5 cycles, at least 10 cycles, at least 20 cycles, or even at least 50 cycles.

Preferably in reusing the ZnO nanoflowers, all of it may be recovered after each purification cycle, enabling several cycles to be repeated with a single batch of ZnO nanoflowers. However, in some embodiments, 0.1-1 mass %, or 1-5 mass % may be lost with each cycle. Preferably the reuse of the ZnO nanoflowers does not change its morphology or other physical characteristics.

Where the ZnO nanoflowers are fixed to single support and exposed to a flowing aqueous solution comprising the aqueous organic contaminant, the used ZnO nanoflowers may be rinsed in place and optionally dried while staying fixed to the support. Alternatively, the ZnO nanoflowers may not be fixed to a support, but confined within a permeable membrane or filter, allowing similar operation.

In one embodiment, all of the above method and characteristics of contaminant reduction may be applied in full or in part to the ZnO nanospheres of the present disclosure.

The examples below are intended to further illustrate protocols for preparing, characterizing, and using the zinc oxide nanospheres and nanoflowers, and are not intended to limit the scope of the claims.

Example 1

Preparation of Zinc Oxide (ZnO) Nanoflowers 0.2 g of zinc nitrate ($Zn(NO_3)_2.6H_2O$) was weighed and transferred into a round bottomed flask with 20 mL deionized water and stirred at room temperature. This was followed by the addition of 0.2 g sodium hydroxide (NaOH) to the flask, which was then stirred for 10 minutes at room temperature. The mixture was then refluxed at 80° C. for 5 hours. The flask was cooled to room temperature and the precipitate was centrifuged, washed with deionized water, and then washed with methanol. The product was dried in an oven for 24 hours at 60° C.

Example 2

Preparation of Zinc Oxide (ZnO) Nanospheres 0.2 g of zinc nitrate ($Zn(NO_3)_2.6H_2O$) was weighed and transferred into a TEFLON-lined autoclave, followed by addition of water (20 mL) and 0.2 g of sodium hydroxide (NaOH). The mixture was stirred at room temperature and then heated at 140° C. for 24 hours. The product was cooled to room temperature, and the precipitate was centrifuged, washed with deionized water, and then washed with methanol. The product was dried at 60° C. in an oven for 24 hours.

Example 3

Physical Characterization

Figure 4:
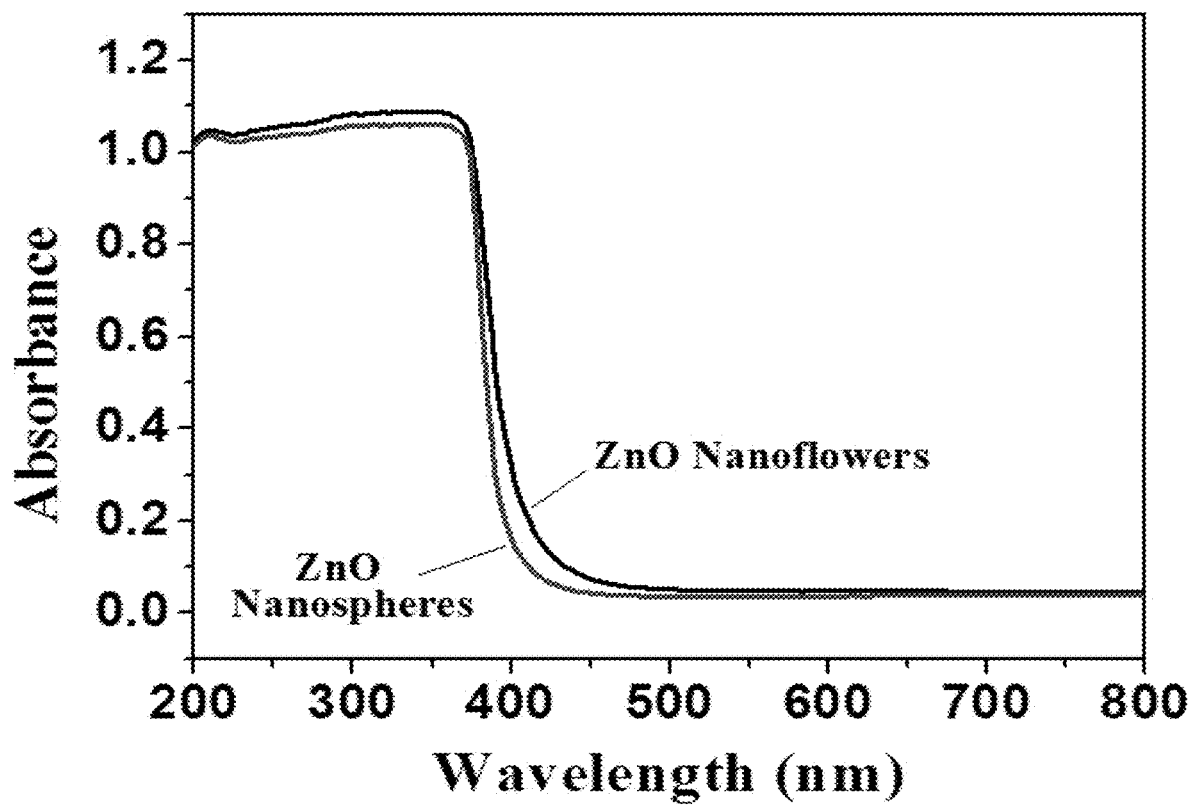
FIG. 4 shows a UV-Vis diffuse reflectance spectrum of ZnO nanoflowers and ZnO nanospheres.
Figure 5:
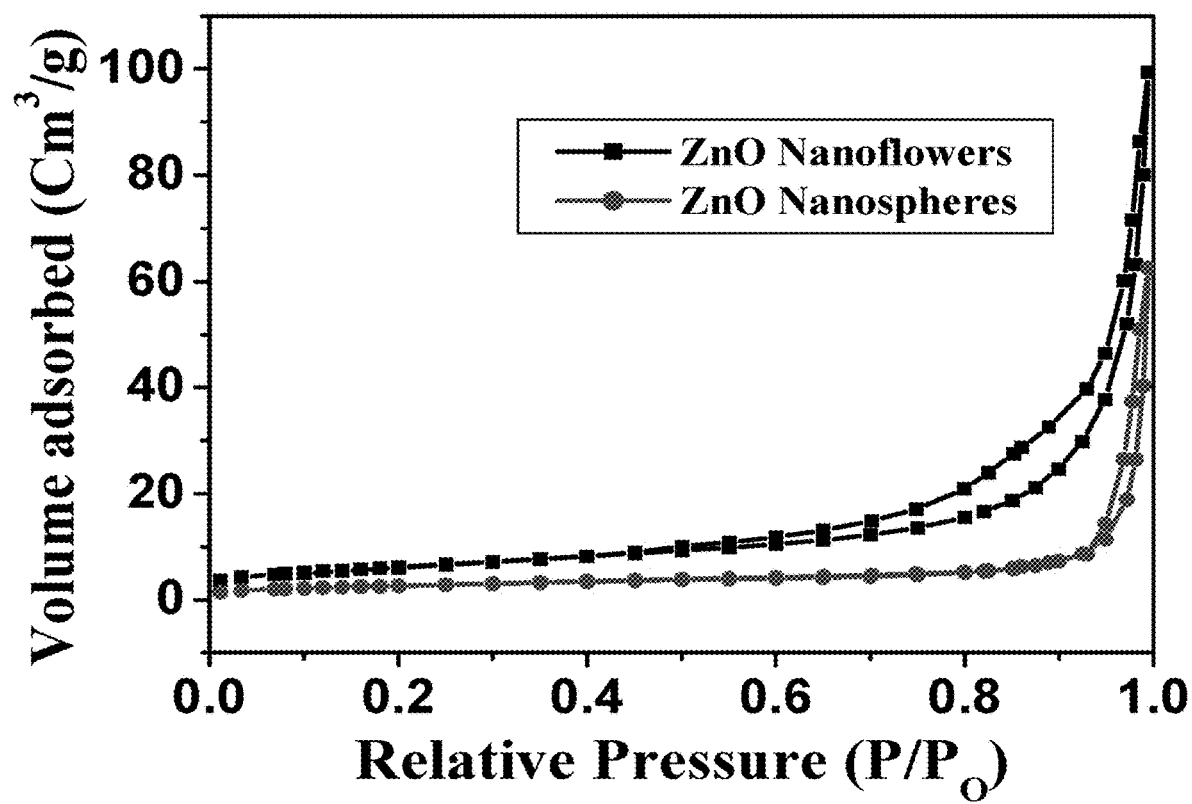
FIG. 5 shows $N_2$ adsorption-desorption isotherms of ZnO nanoflowers and ZnO nanospheres.
Figure 6:
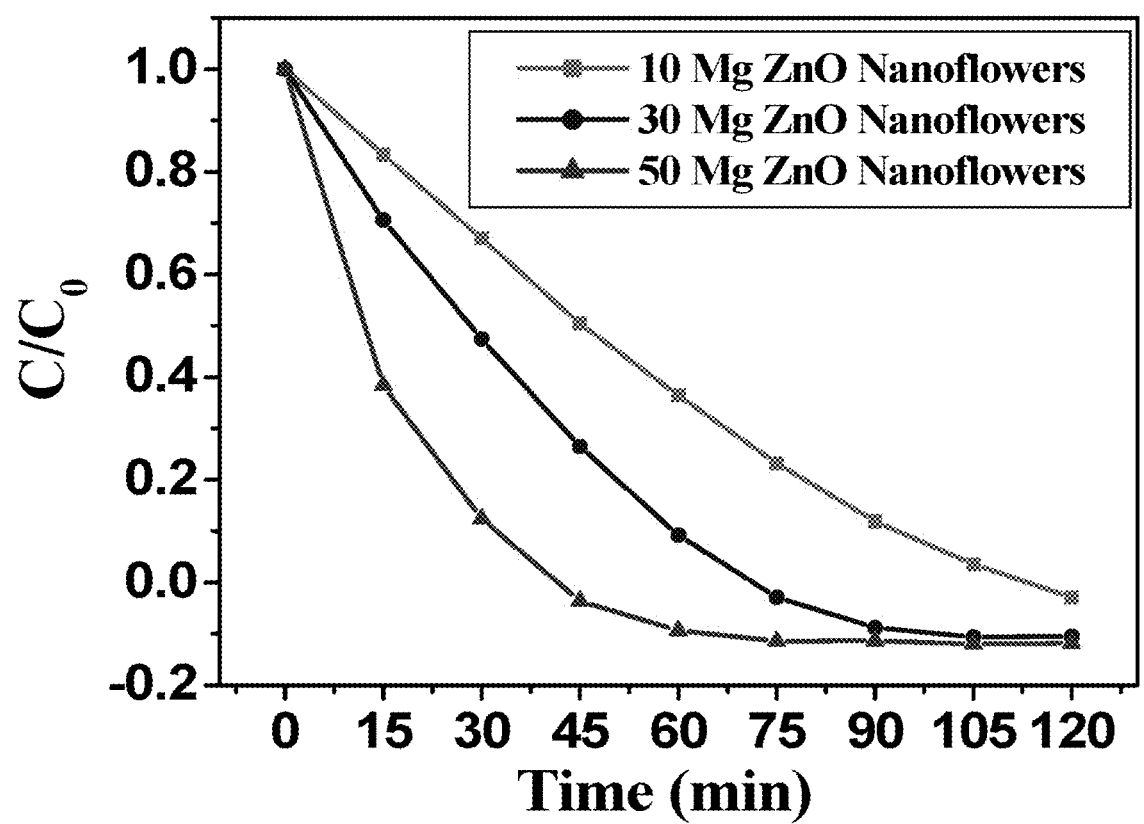
FIG. 6 shows the photocatalytic activities of different amounts of ZnO nanoflowers over 120 minutes.
Figure 7:
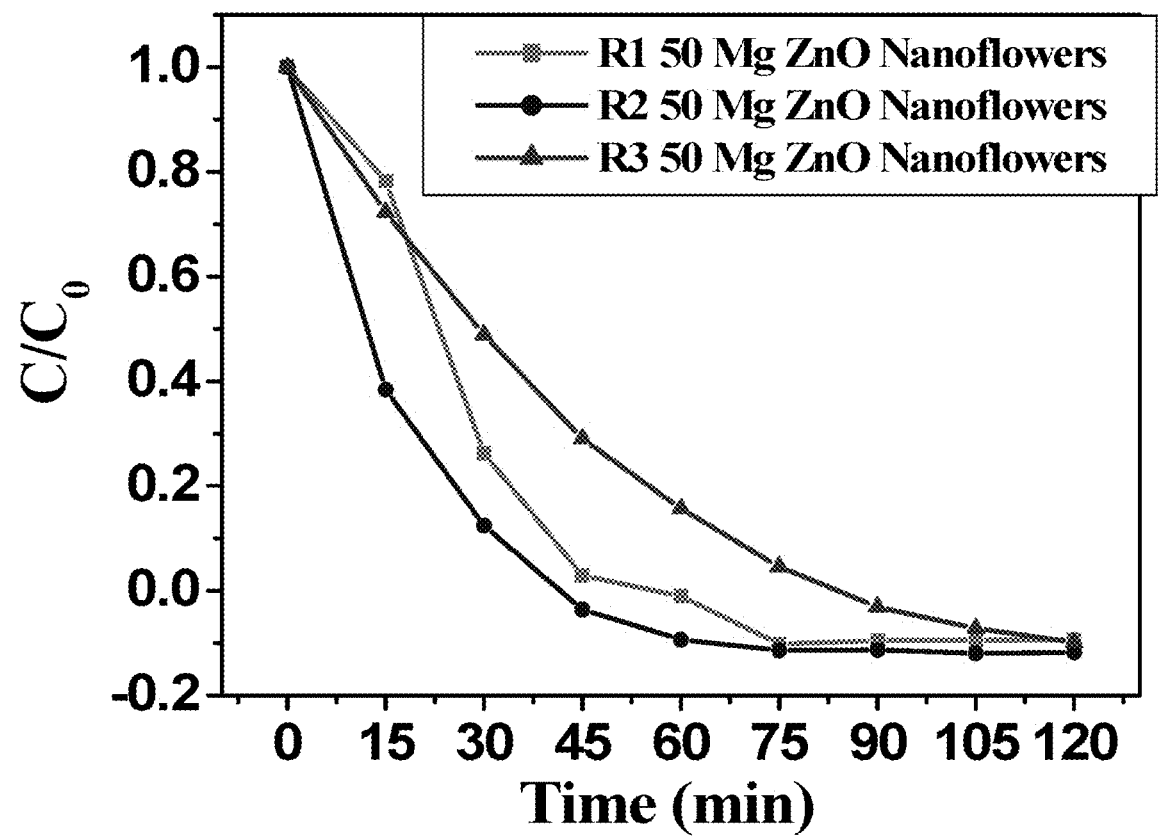
FIG. 7 shows the photocatalytic activities for reusing a 50 mg sample of ZnO nanoflowers.
Figure 8:
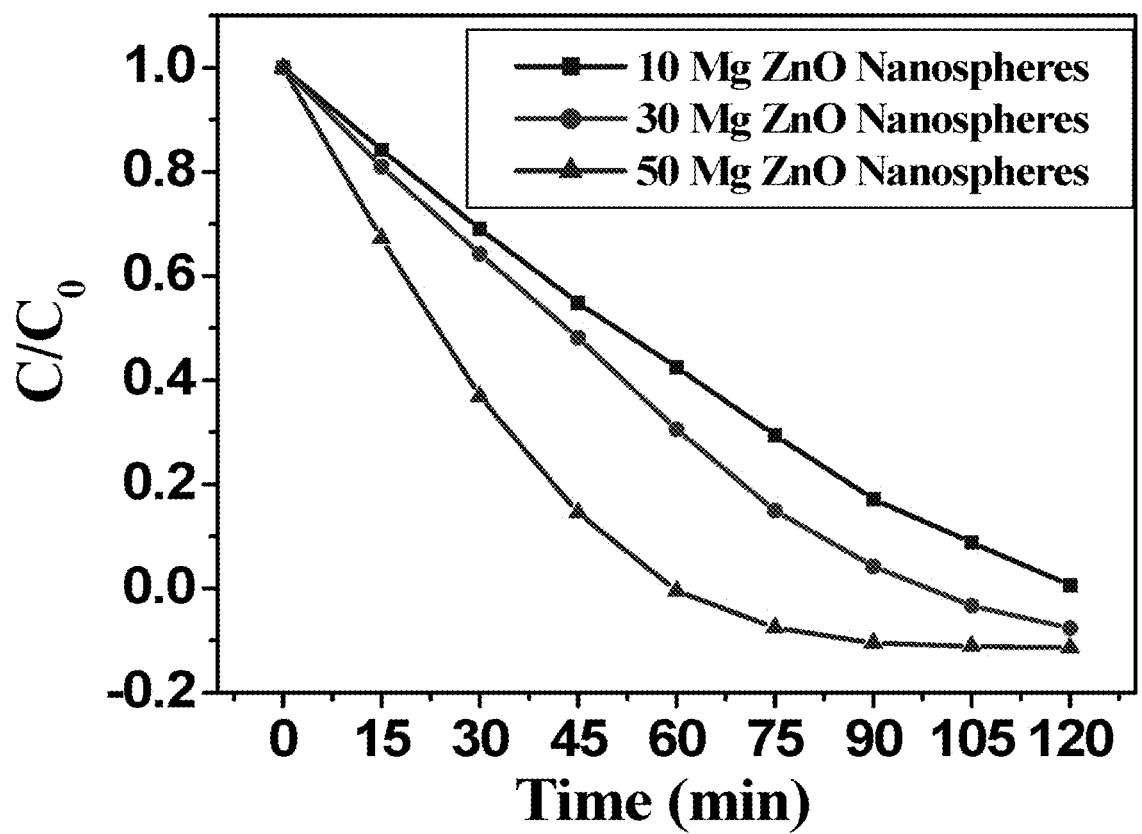
FIG. 8 shows the photocatalytic activities of different amounts of ZnO nanospheres over 120 minutes.
Figure 9:
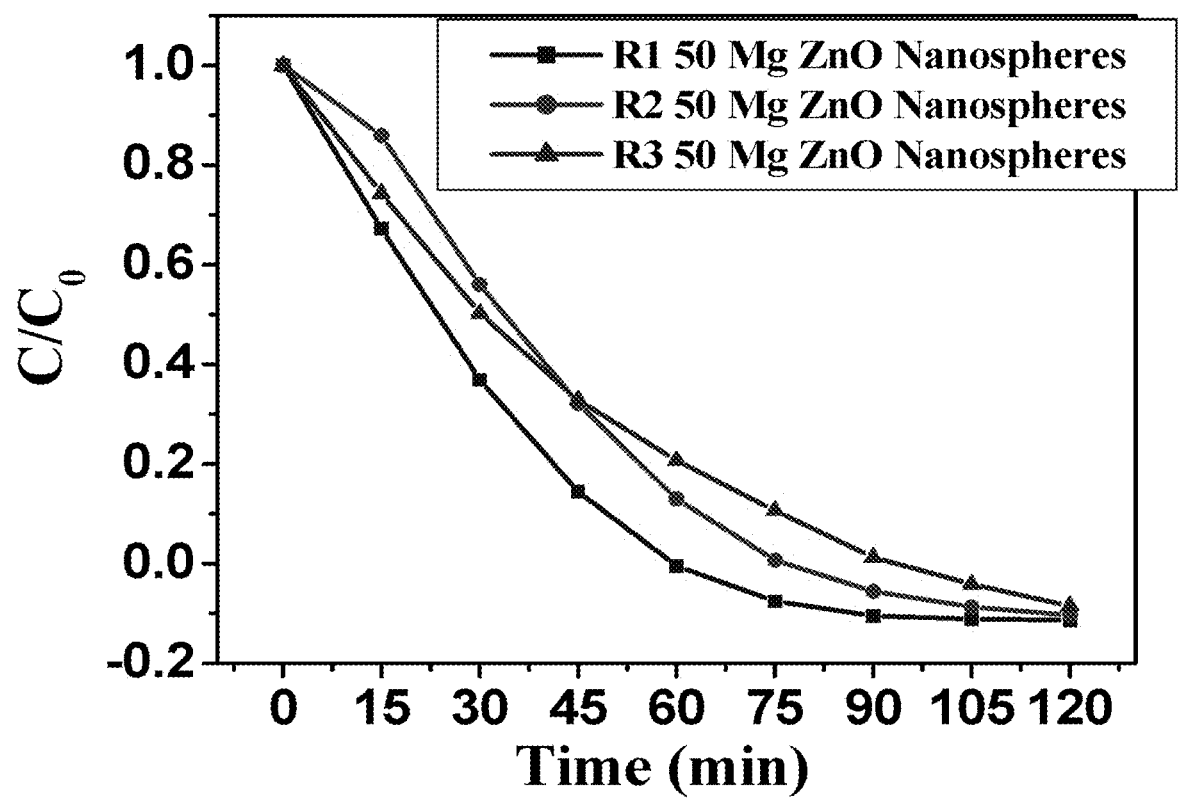
FIG. 9 shows the photocatalytic activities for reusing a 50 mg sample of ZnO nanospheres.

The morphologies of the zinc oxide nanoflowers and nanospheres were examined by scanning electron microscopy (SEM, FEI INSPECT S50), as shown in FIGS. 2A-2B and FIGS. 3A-3B, respectively. The crystallinity and crystal phases of the zinc oxide nanoflowers or nanospheres were studied by an X-ray diffractometer (XRD Rigaku, Japan) using Cu-Kα radiation ($\lambda$=1.5418 Å) in the range of 10°-80° with 1°/min scanning speed. The XRD patterns for both nanoflowers and nanospheres are shown in FIG. 1. UV-Vis diffuse reflectance spectra of zinc oxide nanoflowers and nanospheres, as shown in FIG. 4, were recorded on a diffuse reflectance UV-Vis spectrophotometer (JASCO V-750). Micromeritics ASAP 2020 PLUS nitrogen adsorption apparatus (USA) was employed for BET surface area determination. Before surface area analysis, samples were degassed at 180° C., and the surface area was then determined using $N_2$ adsorption data in the relative pressure ($P/P_0$) range of 0.05-0.3, as shown in FIG. 5. The BET surface area of zinc oxide nanoflowers was observed as 22.54 $m^2/g$ (pore size: 22.92 nm; pore volume 0.1291 $cm^3/g$) while for nanospheres, the surface area was 9.51 $m^2/g$ (pore size: 30.74 nm; pore volume 0.0780 $cm^3/g$).

Example 4

Photocatalytic Activity

Figure 10:
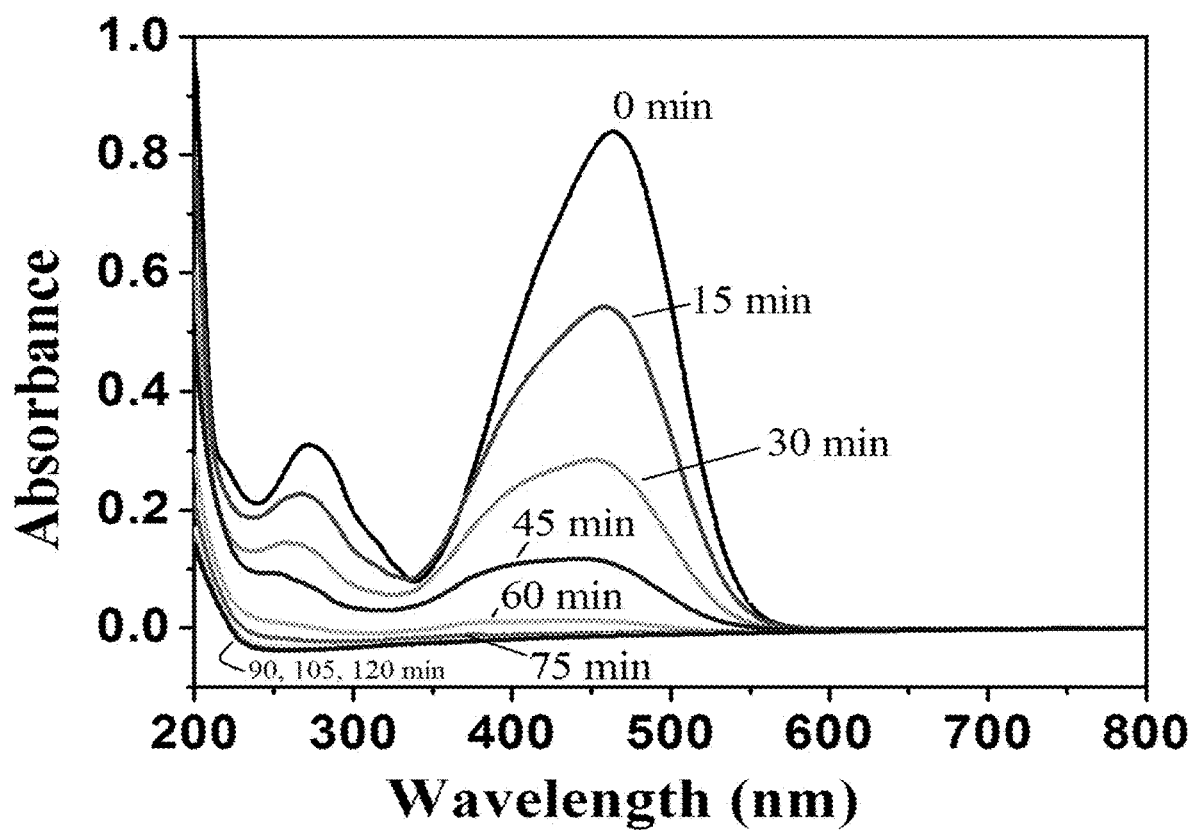
FIG. 10 shows the changes in UV-Vis absorption spectra of methyl orange in the presence of 50 mg ZnO nanoflowers and with different irradiation times.
Figure 11:
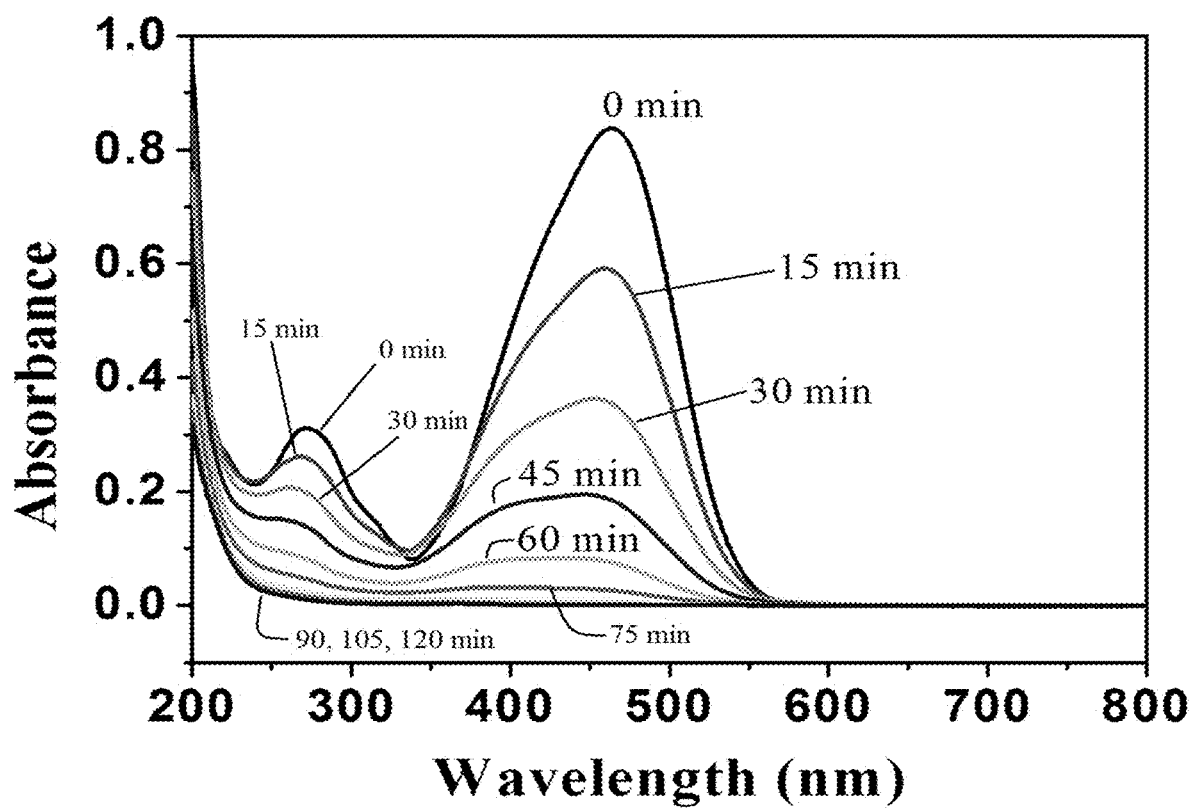
FIG. 11 shows the changes in UV-Vis absorption spectra of methyl orange in the presence of 50 mg ZnO nanospheres and with different irradiation times.

The photocatalytic activity of zinc oxide nanoflowers and nanospheres was evaluated through the photocatalytic degradation of methyl orange under UV light irradiation for 120 min using a xenon lamp (300 W) as the light source. In each experiment, 10 mg, 30 mg, and 50 mg of catalyst (zinc oxide nanoflowers or nanospheres) was dispersed in 100 mL of an aqueous solution of methyl orange dye, the dye having a concentration of 10 mg/L. In order to ensure the adsorption-desorption equilibrium between catalyst and dye, the solution was stirred in the dark for 1 h before irradiating with the xenon lamp. At 15 min time intervals, 4 mL samples of the suspension were collected and centrifuged to remove the zinc oxide nanoflowers or nanospheres, and the concentration of dye in the supernatant was assessed with a UV-Visible spectrophotometer (JASCO V-750) by measuring the absorbance at 465 nm. The change in 200-800 nm absorbance over time is shown in FIGS. 10 and 11. The degradation efficiency was calculated as:

Degradation efficiency (%)=$(C_0-C)/C_0 \times 100\%$, where $C_0$ is the initial concentration of the methyl orange dye, and C is the time-dependent concentration of methyl orange upon irradiation. The change in degradation efficiency over time is shown in FIGS. 6-9.

Example 5

Cell Culture and Cytotoxicity Activity

The human colon cancer cell line HCT116 was purchased from ATTC (American Type Culture Collection, USA) and maintained in DMEM medium. The cytotoxicities of zinc oxide nanoflowers and nanospheres were evaluated against HCT116 cells by MTT assay. The MTT assay was performed with a commercial kit (VYBRANT™ MTT Cell Proliferation Assay Kit, Catalogue no. V13154) from Thermo Fisher Scientific. The colon cancer cells were seeded at a density of $10^4$ cells/well in 96-well plates containing DMEM medium supplemented with 10% fetal bovine serum and 1% antibiotic mixture (Penicillin-Streptomycin). Different amounts of zinc oxide nanoflowers and nanospheres were added to produce final concentrations of 1 mg/mL, 0.4 mg/mL, and 0.2 mg/mL within the wells. The control samples have neither nanoflowers nor nanospheres added. The cells were maintained in a humidified atmosphere with 5% $CO_2$ at 37° C. and were incubated for 24 h. After incubation, the culture medium was removed and the wells were washed twice with phosphate-buffered saline (PBS). After adding fresh medium and 10 μL of MTT solution to each well, the cells were further incubated for 4 h. After incubation, the medium was removed, and 50 μL sterile DMSO was added to each well. The absorbance of each well was recorded on a SYNERGY Neo2 multi-mode microplate reader (Biotek) at 570 nm. The cell viability was then calculated using the following formula:

Cell viability (%)=absorbance of sample/absorbance of control×100%.

Figure 12:
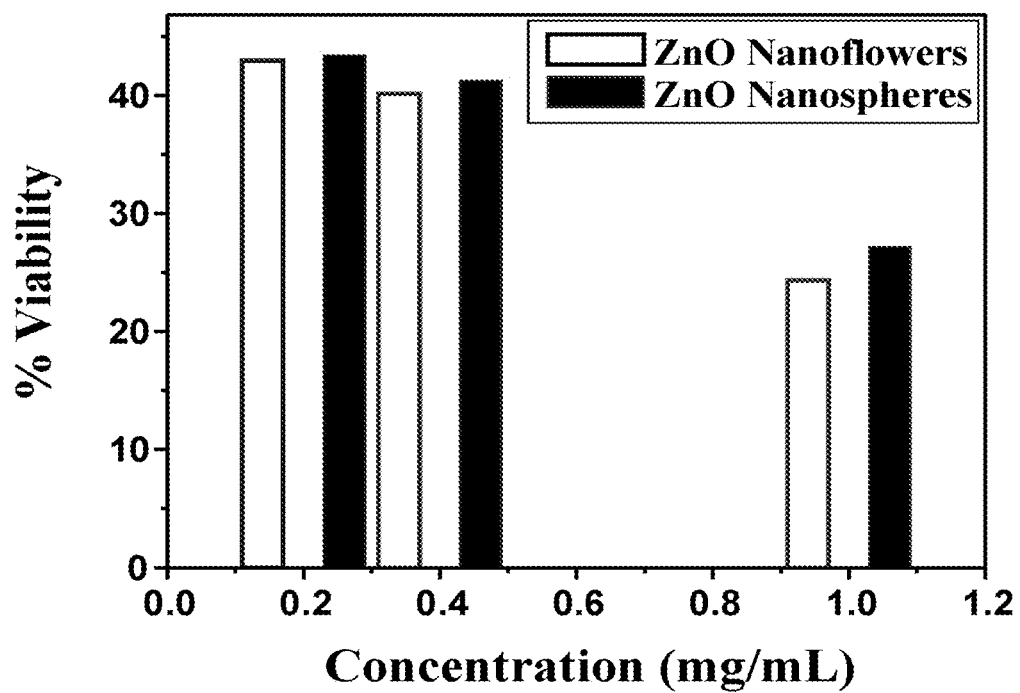
FIG. 12 shows the percent viability of HCT116 cells exposed to different concentrations of ZnO nanoflowers or ZnO nanospheres.

The cell viabilities observed for different amounts of nanospheres and nanoflowers are shown in FIG. 12. This graph shows that higher concentrations of ZnO nanospheres or ZnO nanoflowers lead to lower cell viabilities, which is also an indicator of greater growth inhibition.

The procedures as described above involved different methods for the synthesis of zinc oxide (ZnO) nanoparticles with different morphologies (nanoflowers and nanospheres) and sizes using zinc nitrate hexahydrate as a precursor. The prepared zinc oxide nanoparticles were characterized by X-ray powder diffraction (XRD), scanning electron microscopy (SEM), UV-Vis diffuse reflectance spectrophotometry and BET surface area analysis. The potential application of zinc oxide nanoparticles was evaluated for the (i) photocatalytic degradation of environmental pollutant (Methyl orange), and (ii) biological application (cytotoxicity activity). It was observed that both zinc oxide nanoflowers and nanospheres exhibited good photocatalytic degradation of methyl orange. Cytotoxicity of zinc oxide nanoflowers and nanospheres was evaluated against human colon cancer cell line HCT116 by MTT assay. Both zinc oxide nanoflowers and nanospheres suppressed growth of cancer cells and growth inhibition was 56.62-72.86% and 57.04-75.65% respectively over a range of concentrations (0.2-1 mg/mL).

The invention claimed is:

1. A method of reducing a concentration of an organic contaminant in an aqueous solution, the method comprising:
    contacting ZnO nanoflowers with the aqueous solution comprising the contaminant at a contaminant concentration of 1 mg/L-1 g/L; and
    irradiating the ZnO nanoflowers while in contact with the aqueous solution;
    wherein the ZnO nanoflowers have a generally spherical shape with a diameter of 1.5-3.5 μm,
    wherein a surface of the ZnO nanoflowers has nanopetals of 50-200 nm thickness extending 100-500 nm from the surface, the nanopetals traversing the surface with lengths of 500 nm-2 μm, and
    wherein the ZnO nanoflowers reduce the concentration of the organic contaminant in the aqueous solution by adsorption and/or photocatalytic degradation.

2. The method of claim 1, wherein the ZnO nanoflowers are dispersed within the aqueous solution at a concentration of 0.5-100 mg/L.

3. The method of claim 1, wherein the irradiating is 15-30 minutes of UV light irradiation, and wherein the concentration of the organic contaminant after the irradiating is 40-50% of the concentration of the organic contaminant before the irradiating.

4. The method of claim 1, wherein the organic contaminant is at least one selected from the group consisting of pharmaceutical compound, a dye, a metabolite, a microbial toxin, an herbicide, a pesticide, and a steroid.

5. The method of claim 1, wherein the ZnO nanoflowers are made by heating an aqueous $Zn^{2+}$ solution with sodium hydroxide.

6. The method of claim 5, wherein the aqueous $Zn^{2+}$ solution comprises $Zn(NO_3)_2$.

7. The method of claim 1, wherein the ZnO nanoflowers consist essentially of ZnO.

8. The method of claim 1, wherein the ZnO nanoflowers have a band gap energy of 2.92-3.31 eV.

9. The method of claim 1, wherein the irradiating uses sunlight as an irradiation source.

10. The method of claim 1, further comprising contacting the aqueous solution with a second absorbent or a second photocatalyst to reduce the concentration of the contaminant and/or reduce a concentration of a second contaminant in the aqueous solution.

11. The method of claim 1, further comprising:
    rinsing the ZnO nanoflowers to produce cleaned ZnO nanoflowers; and
    reusing the cleaned ZnO nanoflowers, which maintain a contaminant reduction capacity for at least 5 purification cycles.

* * * * *